US011938311B2

(12) United States Patent
Corbett et al.

(10) Patent No.: US 11,938,311 B2
(45) Date of Patent: Mar. 26, 2024

(54) ANTI-SUCTION BLOOD PUMP INLET

(71) Applicant: ABIOMED, Inc., Danvers, MA (US)

(72) Inventors: Scott C. Corbett, Danvers, MA (US);
Ahmad El Katerji, Danvers, MA (US);
Charles DeLorenzo, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 17/410,168

(22) Filed: Aug. 24, 2021

(65) Prior Publication Data
US 2022/0040472 A1   Feb. 10, 2022

Related U.S. Application Data

(63) Continuation of application No. 15/694,134, filed on Sep. 1, 2017, now Pat. No. 11,123,541.
(Continued)

(51) Int. Cl.
*A61M 60/857* (2021.01)
*A61M 60/13* (2021.01)
(Continued)

(52) U.S. Cl.
CPC .......... *A61M 60/422* (2021.01); *A61M 60/13* (2021.01); *A61M 60/226* (2021.01); *A61M 60/443* (2021.01); *A61M 60/857* (2021.01)

(58) Field of Classification Search
CPC .............. A61M 60/857; A61M 60/174; A61M 60/178; A61M 60/216; A61M 60/226
See application file for complete search history.

(56) References Cited

U.S. PATENT DOCUMENTS

| 5,921,913 A | 7/1999 | Siess |
| 6,248,091 B1 | 6/2001 | Voelker |
| (Continued) | | |

FOREIGN PATENT DOCUMENTS

| EP | 1317295 A1 | 6/2003 |
| JP | H11239617 A | 9/1999 |
| (Continued) | | |

OTHER PUBLICATIONS

International Preliminary Report on Patentability from International Application No. PCT/US2017/049879, dated Mar. 5, 2019, 7 pp.
(Continued)

*Primary Examiner* — George R Evanisko
(74) *Attorney, Agent, or Firm* — Botos Churchill IP Law LLP

(57) ABSTRACT

A heart pump assembly includes an impeller blade coupled to a rotor or a drive shaft, a cannula, a distal projection coupled to a distal end of the cannula and a blood inlet having a plurality of apertures. The plurality of apertures is radially oriented and disposed about a circumference of the cannula. The plurality of apertures includes at least a first ring of apertures which are proximal to the distal projection and a second ring of apertures which are proximal of the first ring of apertures. The plurality of apertures can allow the heart pump assembly to continue to function if anatomical structures or tissue become suctioned to a portion of the heart pump.

16 Claims, 18 Drawing Sheets

Related U.S. Application Data

(60) Provisional application No. 62/382,471, filed on Sep. 1, 2016.

(51) Int. Cl.
*A61M 60/226* (2021.01)
*A61M 60/422* (2021.01)
*A61M 60/443* (2021.01)

(56) References Cited

U.S. PATENT DOCUMENTS

| | | | |
|---|---|---|---|
| 6,544,216 | B1 | 4/2003 | Sammler et al. |
| 6,808,508 | B1* | 10/2004 | Zafirelis .............. A61M 1/3659 604/6.11 |
| 7,022,100 | B1 | 4/2006 | Aboul-Hosn et al. |
| 8,888,728 | B2 | 11/2014 | Aboul-Hosn et al. |
| 9,327,068 | B2 | 5/2016 | Aboul-Hosn et al. |
| 9,545,468 | B2 | 1/2017 | Aboul-Hosn et al. |
| 9,561,314 | B2 | 2/2017 | Aboul-Hosn et al. |
| 9,597,437 | B2 | 3/2017 | Aboul-Hosn et al. |
| 9,789,238 | B2 | 10/2017 | Aboul-Hosn et al. |
| 9,833,550 | B2 | 12/2017 | Siess |
| 9,872,948 | B2 | 1/2018 | Siess |
| 10,238,783 | B2 | 3/2019 | Aboul-Hosn et al. |
| 11,123,541 | B2* | 9/2021 | Corbett ............... A61M 60/226 |
| 2003/0124007 | A1 | 7/2003 | Schima et al. |
| 2003/0187322 | A1* | 10/2003 | Siess ................... A61M 60/554 600/16 |
| 2005/0085772 | A1 | 4/2005 | Zafirelis et al. |
| 2010/0022939 | A1 | 1/2010 | Schima et al. |
| 2010/0041939 | A1 | 2/2010 | Siess |
| 2010/0268017 | A1 | 10/2010 | Siess |
| 2011/0004046 | A1* | 1/2011 | Campbell ............. A61M 60/13 600/16 |
| 2013/0303969 | A1 | 11/2013 | Keenan et al. |
| 2014/0364880 | A1 | 12/2014 | Farnan et al. |
| 2015/0328383 | A1 | 11/2015 | Corbett et al. |
| 2017/0340791 | A1 | 11/2017 | Aboul-Hosn et al. |

FOREIGN PATENT DOCUMENTS

| | | | |
|---|---|---|---|
| JP | 2002518106 | A | 6/2002 |
| JP | 2004506490 | A | 3/2004 |
| JP | 2007501644 | A | 2/2007 |
| JP | 2008519624 | A | 6/2008 |
| JP | 2010521261 | A | 6/2010 |
| JP | 2015514529 | A | 5/2015 |
| WO | 9965546 | A1 | 12/1999 |
| WO | 0117581 | A2 | 3/2001 |
| WO | 0215963 | A1 | 2/2002 |
| WO | 2005016416 | A1 | 2/2005 |
| WO | 2006051023 | A1 | 5/2006 |
| WO | 2009099644 | A1 | 8/2009 |
| WO | 2010008560 | A1 | 1/2010 |
| WO | 2013160407 | A1 | 10/2013 |
| WO | 2015175711 | A1 | 11/2015 |
| WO | 2016034171 | A2 | 3/2016 |

OTHER PUBLICATIONS

Office Action from corresponding Israeli Patent Application No. 264885 dated Dec. 5, 2021 (7 pages).
Office Action for corresponding EP Application No. 17 768 315.8 dated Jun. 15, 2022 (5 pages).
Australian Examination Report for Application No. 2017318694, dated Oct. 2, 2021.
Notice of Reasons for Rejection in Japanese Patent Application No. 2019-511853, dated Sep. 15, 2021.
International Search Report for PCT Application No. PCT/US2017/049879, dated Nov. 29, 2017.
Siess, "Systems Analysis and Development of Intravascular Rotation Pumps for Heart Support," Reports from Biomedical Technology, vol. 6, Shaker Verlag (1999).
Temporary Cardiac Assist with an Axial Pump System (W. Flameng) Ann Thorac Surg 1990a, 49:299-304 and Steinkopff Verlag Damstadt/ Springer-Verlag New York, 1991.
Communication from corresponding European Patent Application No. 17 768 315.8 dated Nov. 23, 2021 (5 pages).
Office Action from Israeli Patent Application No. 294806, dated Nov. 9, 2022 (4 pages).
Office Action from corresponding European Patent Application No. 17768315.8 dated Jun. 7, 2023 (4 pp.).
Office Action from corresponding Japanese Patent Application No. 2022-113632 dated May 22, 2023 (9 pp.).
Office Action issued in Australian Patent Application No. 2022215276 dated Oct. 16, 2023 (5 pp.).
Decision to Grant for Japanese Patent Application No. 2022-113632 dated Nov. 15, 2023 (6 pp.).

* cited by examiner

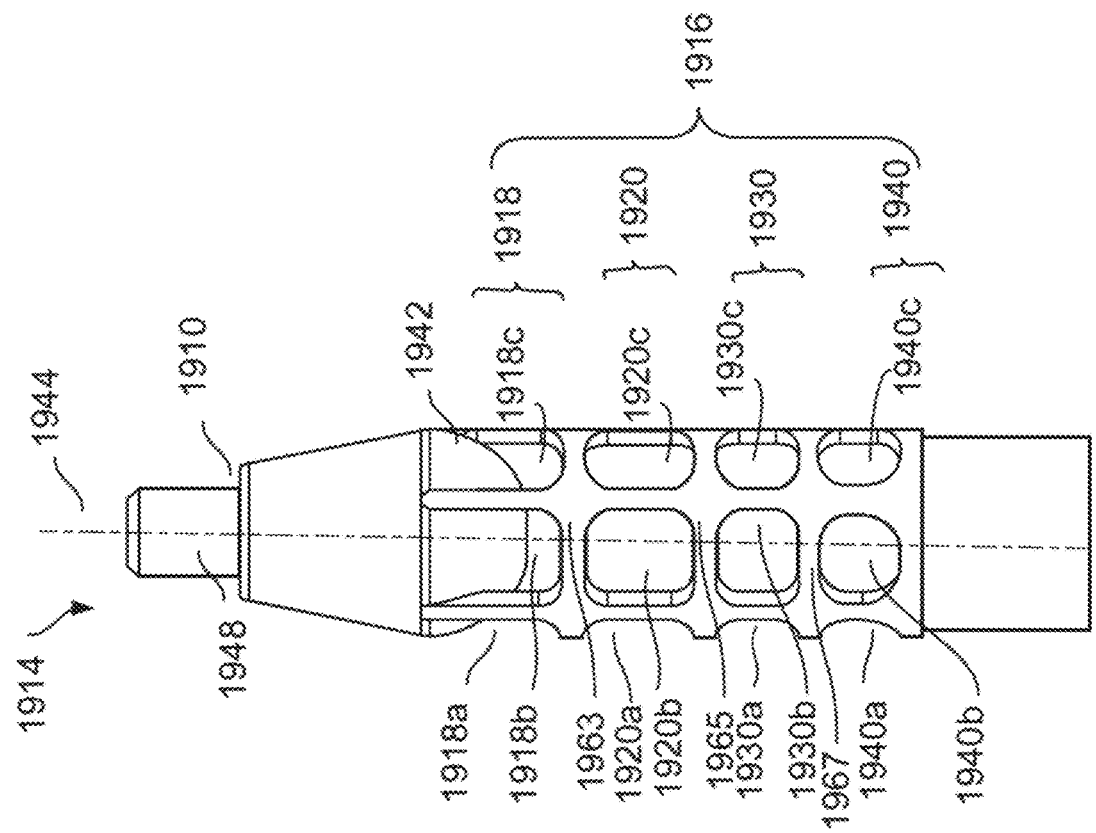
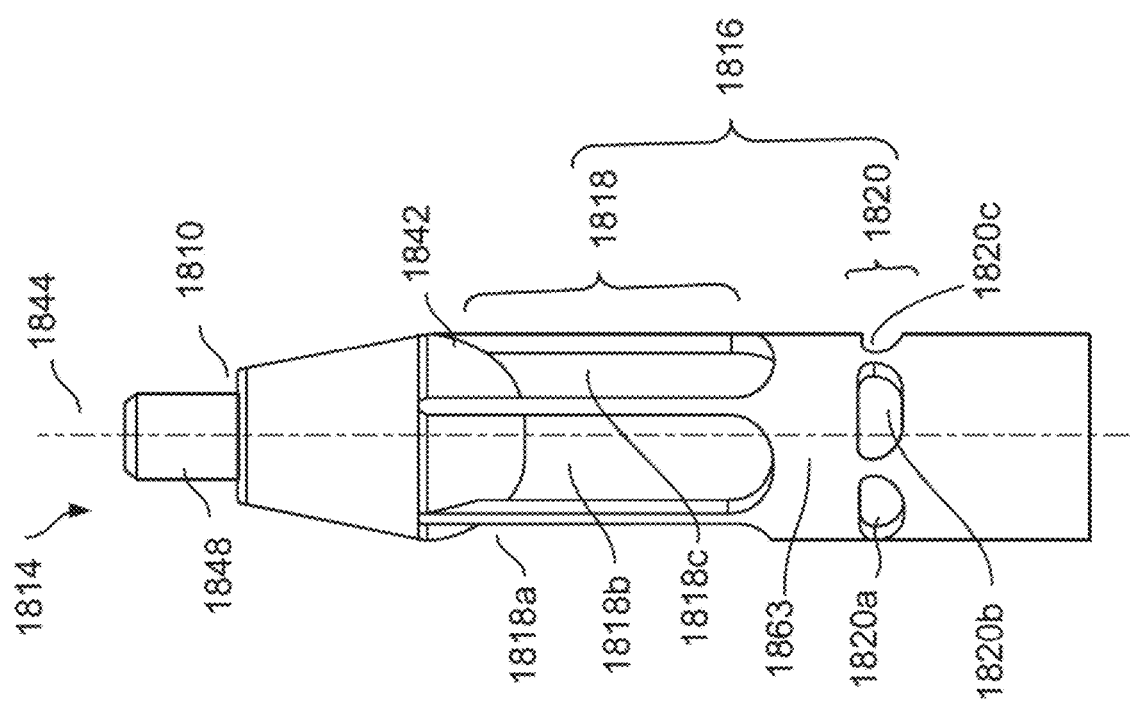

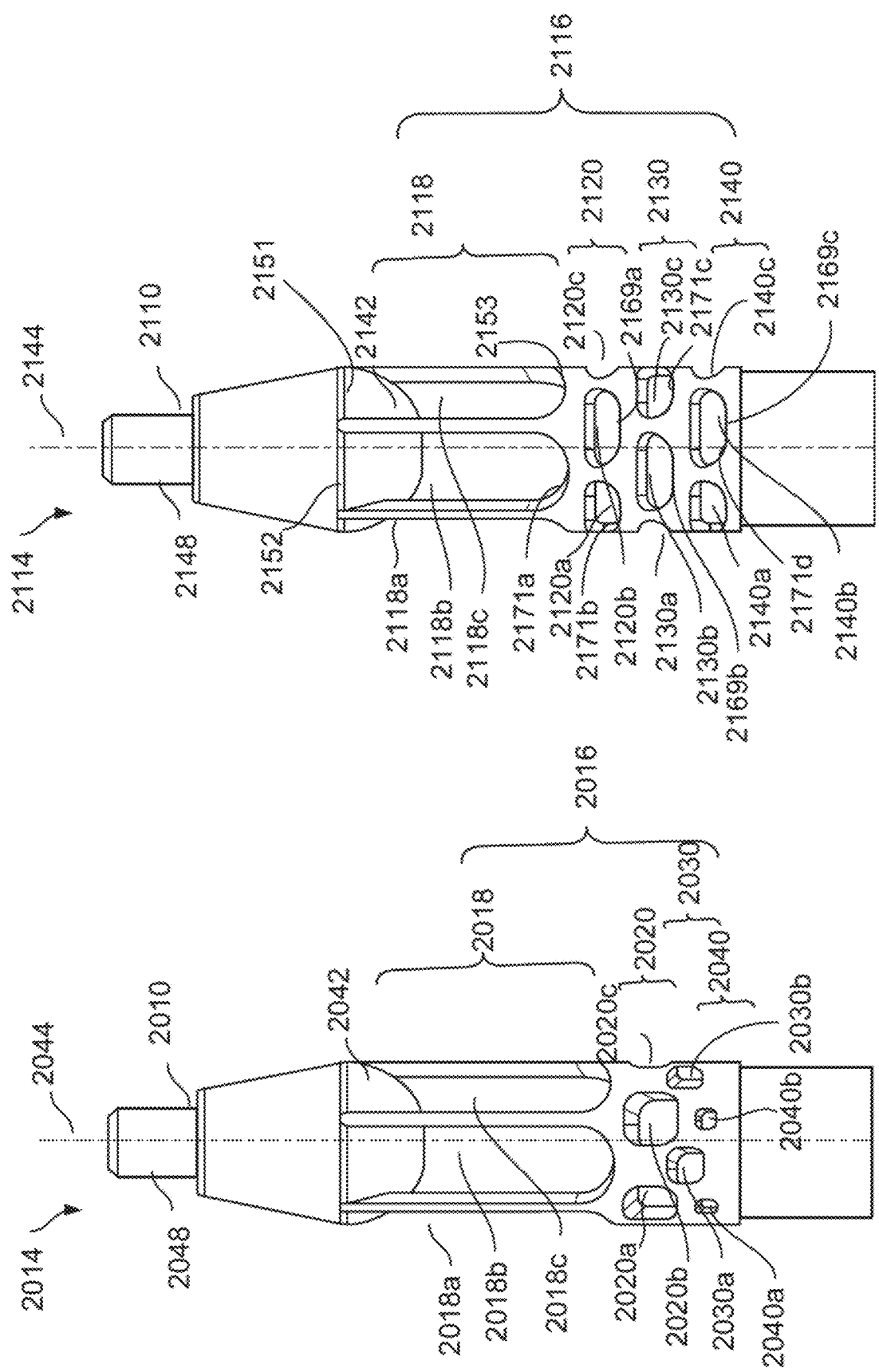

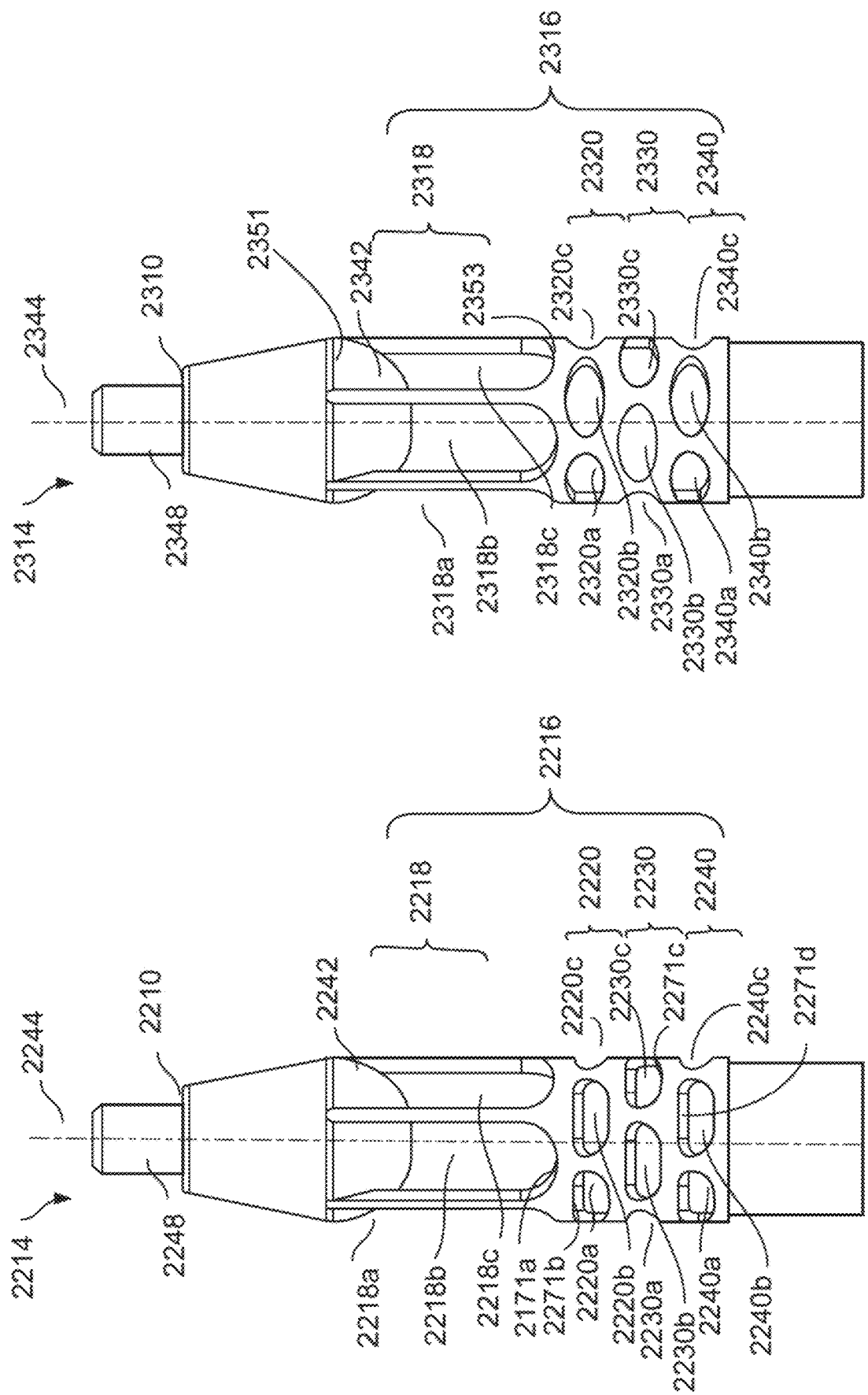

ANTI-SUCTION BLOOD PUMP INLET

CROSS-REFERENCE TO RELATED APPLICATIONS

The present application is a continuation of U.S. patent application Ser. No. 15/694,134, filed Sep. 1, 2017, now U.S. Pat. No. 11,123,541, which claims the benefit of U.S. Provisional Patent Application No. 62/382,471, filed Sep. 1, 2016, the disclosures of which are incorporated herein by reference in their entirety.

BACKGROUND

A heart pump, such as a percutaneous intracardiac heart pump assembly, can be introduced in the heart to deliver blood from the heart into an artery. When deployed in the heart, a heart pump assembly pulls blood from the left ventricle of the heart and expels blood into the aorta, or pulls blood from the right ventricle and expels blood into the pulmonary artery. Some heart pump assemblies pull blood through inflow apertures into a cannula and expel the blood from the cannula into the aorta through outflow apertures. Sometimes the inflow apertures suck against the interior of the ventricle in which they are located or against other structures such as the mitral valve and/or chordae. When this suction occurs, the flow of blood into the pump and/or through the cannula is blocked or impeded, lessening the assistance provided to the heart.

SUMMARY

Systems, devices, and methods described herein provide heart pump assemblies with improved inflow apertures. The inflow apertures are designed to prevent or reduce the tendency of the inflow aperture to suck against the interior of the heart or vascular system of a patient. In particular, the inflow apertures can prevent the pump inlet from sucking a valve leaflet (e.g., a leaflet of the mitral valve) into the inlet. This can reduce the risk of occlusion of the apertures to allow the pump to provide more blood pumping assistance to the heart. The improved apertures may also decrease the risk of damage to structures of the heart which may be suctioned to the pump.

The heart pump includes a plurality of inflow apertures. The inflow apertures can be disposed at a distal end portion of a cannula of the heart pump (e.g., in the case of pumps designed to assist the left ventricle). The inflow apertures can be arranged in two or more rings or rows that are offset from one another along a longitudinal axis of the pump. The use of multiple rings or rows of apertures, rather than a single ring of apertures, can allow each aperture to be smaller, which may reduce the risk that heart structures (e.g., valves) will enter the inlet through the apertures. Furthermore, the additional inflow apertures provide redundancy so that if one subset of the apertures is blocked, there are additional apertures through which blood can enter the pump. The outer edges of the apertures can be defined by struts coupled to the cannula. The struts can function as a screen to prevent the suction of valve leaflets against or into the pump.

In one aspect, a heart pump assembly includes a rotor, a motor coupled to the rotor, an impeller blade coupled to the rotor such that rotation of the rotor causes the impeller blade to rotate and pump blood, a cannula, a distal projection coupled to a distal end of the cannula, and a blood inlet including a plurality of apertures radially oriented and disposed about a circumference thereof. The plurality of apertures includes at least a first ring of apertures which are proximal to the atraumatic tip and a second ring of apertures which are proximal of the first ring of apertures.

In some implementations, a first aperture in the first ring of apertures has a greater area than an area of a second aperture in the second ring of apertures. In some implementations, the first apertures in the first ring of apertures and the second ring in the second ring of apertures are oblong. In some implementations, the heart pump assembly includes a third ring of apertures proximal of the second ring. In some implementations, the heart pump assembly includes a fourth ring of apertures proximal of the third ring.

In some implementations, the first aperture in the first ring of apertures and a third aperture in the third ring of apertures are aligned along an axis on a surface of the cannula parallel to a longitudinal axis of the cannula. In some implementations, the second aperture in the second ring of apertures is aligned with a fourth aperture in the fourth ring of apertures along the axis on the surface of the cannula parallel to the longitudinal axis of the cannula.

In some implementations, the first aperture in the first ring of apertures has a height measured parallel to the longitudinal axis of the cannula that is greater than a height of any of the second aperture, third aperture or fourth aperture. In some implementations, the height of the first apertures is less than 9 mm. In some implementations, the height of the second aperture is less than 3 mm. In some implementations, a width of the second aperture is less than 4 mm. In some implementations, an area of the first aperture is less than 20 $mm^2$. In some implementations, an area of the second aperture is less than 12 $mm^2$. In some implementations, the plurality of apertures is formed on an inflow cage that is coupled to the cannula. In some implementations, the inflow cage is comprised of stainless steel. In some implementations, the plurality of apertures is formed near a terminal end of the cannula.

In some implementations, some of the pluralities of apertures are oblong. In some implementations, some of the pluralities of apertures are round. In some implementations, some of the pluralities of apertures are tear-shaped with a rounded edge oriented at a distal end of the each of the apertures and a pointed edge oriented at a proximal side of each of the apertures. In some implementations, a first aperture in the first ring of apertures has a smaller area than a second aperture in the second ring of apertures. In some implementations, a first aperture in the first ring of apertures has the same area than a second aperture in the second ring of apertures. In some implementations, the distal end portion of the cannula comprises an inflow cage. In some implementations, a distal edge of the first aperture is formed by a base of the atraumatic tip.

In some implementations, each of the plurality of apertures is defined by an inner edge intersecting an interior of the cannula and an outer edge intersecting the surface of the cannula. In some implementations, the outer edge of each of the plurality of apertures is rounded. In some implementations, the outer edge of each of the plurality of apertures is chamfered. In some implementations, the heart pump assembly is sized for percutaneous insertion.

In another aspect, a heart pump assembly includes a rotor, a motor coupled to the rotor, an impeller blade coupled to the rotor such that rotation of the rotor causes the impeller blade to rotate and pump blood, a cannula, and a blood inlet including a plurality of apertures radially oriented and disposed about a circumference thereof. The plurality of apertures includes at least a first ring of apertures and a second ring of apertures, the second ring being proximal of the first ring of apertures. In the plurality of apertures, each aperture of the first ring of apertures has a greater area than an aperture of the second ring of apertures.

In some implementations, the first apertures in the first ring of apertures and the second ring in the second ring of apertures are oblong. In some implementations, the heart pump assembly includes a third ring of apertures proximal of the second ring. In some implementations, the heart pump assembly includes a fourth ring of apertures proximal of the third ring. In some implementations, the first aperture in the first ring of apertures and a third aperture in the third ring of apertures are aligned along an axis on a surface of the cannula parallel to a longitudinal axis of the cannula. In some implementations, the second aperture in the second ring of apertures is aligned with a fourth aperture in the fourth ring of apertures along the axis on the surface of the cannula parallel to the longitudinal axis of the cannula.

In some implementations, the first aperture in the first ring of apertures has a height measured parallel to the longitudinal axis of the cannula that is greater than a height of any of the second aperture, third aperture or fourth aperture. In some implementations, the height of the first apertures is less than 9 mm. In some implementations, the height of the second aperture is less than 3 mm. In some implementations, a width of the second aperture is less than 4 mm. In some implementations, an area of the first aperture is less than 20 mm². In some implementations, the plurality of apertures is formed on an inflow cage that is coupled to the cannula. In some implementations, the inflow cage is comprised of stainless steel. In some implementations, the plurality of apertures is formed near a terminal end of the cannula.

In some implementations, each of the plurality of apertures is defined by an inner edge intersecting an interior of the cannula and an outer edge intersecting the surface of the cannula. In some implementations, the outer edge of each of the plurality of apertures is rounded. In some implementations, the outer edge of each of the plurality of apertures is chamfered. In some implementations, the heart pump assembly is sized for percutaneous insertion.

In another aspect, a method of manufacturing a heart pump assembly includes coupling an impeller blade to a rotor, inserting the impeller blade in a housing, coupling a cannula to the housing, and coupling an inflow cage including a plurality of apertures to the cannula. The plurality of apertures is radially oriented about a circumference of the inflow cage and the plurality of apertures are arranged in at least a first ring of apertures and a second ring of apertures proximal of the first ring of apertures.

In some implementations, the inflow cage comprises a third ring of apertures proximal of the second ring of apertures. In some implementations, the inflow cage comprises a fourth ring of apertures proximal of the third ring of apertures. In some implementations, each of the plurality of apertures includes an outer edge formed by a tumbling process. In some implementations, the plurality of apertures is formed near a terminal end of the cannula. In some implementations the method also includes coupling a distal projection to the distal end of the inflow cage. The distal projection is distal to the plurality of apertures and a base of the distal projection forms a distal edge of the first ring of apertures.

In another aspect, a method of operating a heart pump assembly includes rotating an impeller about a rotation axis using a motor to draw blood into a cannula of a heart pump assembly at a plurality of blood inlet apertures, and expelling the blood from the heart pump assembly via a plurality of blood exhaust apertures disposed at a proximal end portion of the cannula proximal to the pump. The blood inlet apertures are radially oriented about a circumference of the cannula and arranged in at least two rings at a distal end of the cannula.

Variations and modifications will occur to those of skill in the art after reviewing this disclosure. The disclosed features may be implemented, in any combination and subcombination (including multiple dependent combinations and subcombinations), with one or more other features described herein. For example, although various specific arrangements of apertures are described herein, a heart pump assembly may be configured to have any number of apertures arranged in any suitable number of rings. Further, the apertures may have any suitable size, shape, or position. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 18 shows a front view of a distal end portion of a heart pump assembly having an alternative arrangement of apertures positioned in a first ring of long apertures and a second ring of shorter apertures spaced apart from the first ring, in accordance with example implementations;

FIG. 19 shows a front view of a distal end portion of a heart pump assembly having an alternative arrangement of apertures positioned in four rings of similarly sized apertures, in accordance with example implementations;

FIG. 20 shows a front view of a distal end portion of a heart pump assembly having an alternative arrangement of apertures positioned in four rings of differently sized apertures, in accordance with example implementations;

FIG. 21 shows a front view of a distal end portion of a heart pump assembly having an alternative arrangement of apertures having chamfered edges, in accordance with example implementations;

FIG. 22 shows a front view of a distal end portion of a heart pump assembly having an alternative arrangement of apertures with rounded edges, in accordance with example implementations;

FIG. 23 shows a front view of a distal end portion of a heart pump assembly having an alternative arrangement of apertures, in accordance with example implementations;

DETAILED DESCRIPTION

To provide an overall understanding of the systems, methods, and devices described herein, certain illustrative embodiments will be described. Although the embodiments and features described herein are described with reference to specific numbers, sizes, and shapes of apertures, it will be understood that the heart pump assembly may be configured to have any suitable number of apertures arranged in any number of rings, not limited to the arrangements described here. Additionally, the apertures may have any suitable size, shape, or position.

Systems, devices, and methods described herein provide heart pump assemblies with improved inflow apertures. The inflow apertures are designed to prevent or reduce the tendency of the inflow aperture to suck against the interior of the heart or vascular system of the patient. In particular, the inflow apertures can prevent the pump inlet from sucking a valve leaflet (e.g., a leaflet of the mitral valve) into the inlet. This can reduce the risk of occlusion of the apertures to allow the pump to provide more blood pumping assistance to the heart. The improved apertures may also decrease the risk of damage to structures of the heart which may be suctioned to the pump The heart pump includes a plurality of inflow apertures. The inflow apertures can be disposed at a distal end portion of a cannula of the heart pump (e.g., in the case of pumps designed to assist the left ventricle). The inflow apertures can be arranged in two or more rings or rows that are offset from one another along a longitudinal axis of the pump. The use of multiple rings or rows of apertures, rather than a single ring of apertures can allow each aperture to be smaller, which may reduce the risk that heart structures (e.g., valves) will enter the inlet through the apertures. Furthermore, the additional inflow apertures provide redundancy so that if one subset of the apertures is blocked, there are additional apertures through which blood can enter. The outer edges of the apertures can be defined by struts coupled to the cannula. The struts can function as a screen to prevent the suction of valve leaflets against or into the apertures.

Figure 1:
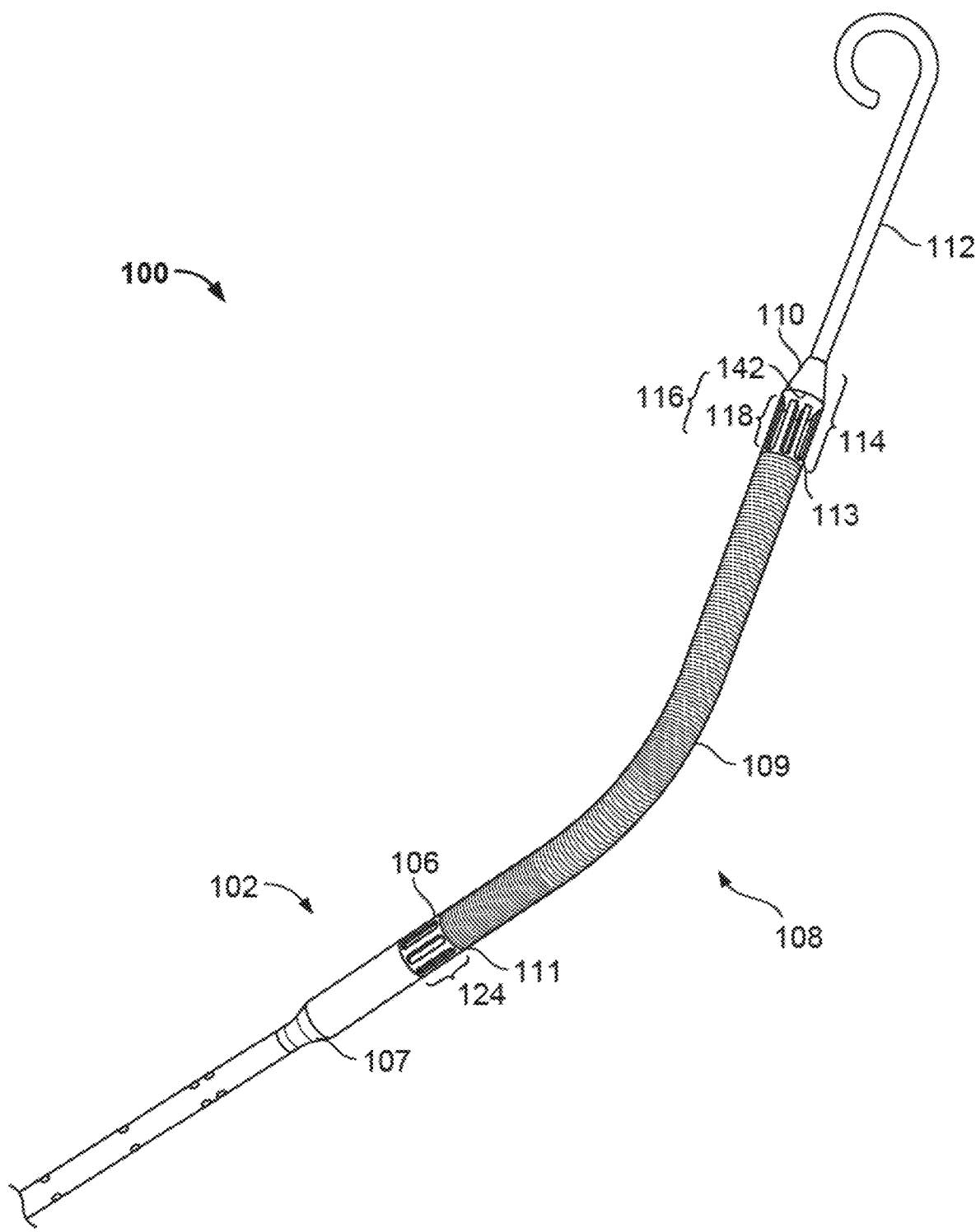
FIG. 1 shows an exemplary prior art heart pump assembly.

FIG. 1 shows an exemplary prior art heart pump assembly 100. The heart pump assembly 100 includes a motor housing 102, a cannula assembly 108, a plurality of apertures 116, a plurality of blood exhaust outlets 124, and a projection or atraumatic tip 112. The cannula assembly 108 has a proximal end 111, a cannula body 109, an inflow cage 113, a distal end 110, a distal end portion 114, and a tear drop portion 142. The motor housing 102 has a proximal end 107 and a distal end 106. The plurality of apertures 116 are arranged in a single ring 118 in the inflow cage 113 at the distal end portion 114 of the cannula assembly 108. The atraumatic tip 112 is coupled to the cannula assembly 108 at the distal end 110 of the cannula assembly 108 at the tear drop portion 142.

The heart pump assembly 100 pulls blood through the plurality of apertures 116 and into the cannula assembly 108. The pump expels the blood proximal of the proximal end 111 of the cannula assembly 108 through the plurality of blood exhaust apertures 124. The heart pump assembly 100 may be percutaneously inserted into the heart through the aorta. The plurality of apertures 116 may be positioned past the aortic valve in the left ventricle, in order to pull blood from the left ventricle and expel the blood into the aorta. Although the atraumatic tip 112 spaces the heart pump assembly 100 from the heart walls, in some instances the plurality of apertures 116 may be positioned near to the walls of the heart or various heart structures, such as the leaflets of the mitral valve. The plurality of apertures 116 each have a large area which may suction structures of the heart, such as valve leaflets against the apertures 116 and even through the apertures 116 into the cannula assembly 108. This can block some or all of the inflow of blood into the cannula assembly 108. When the flow of blood through the cannula assembly 108 is blocked, the support that the heart pump assembly 100 can provide to the heart is lessened.

Figure 2:
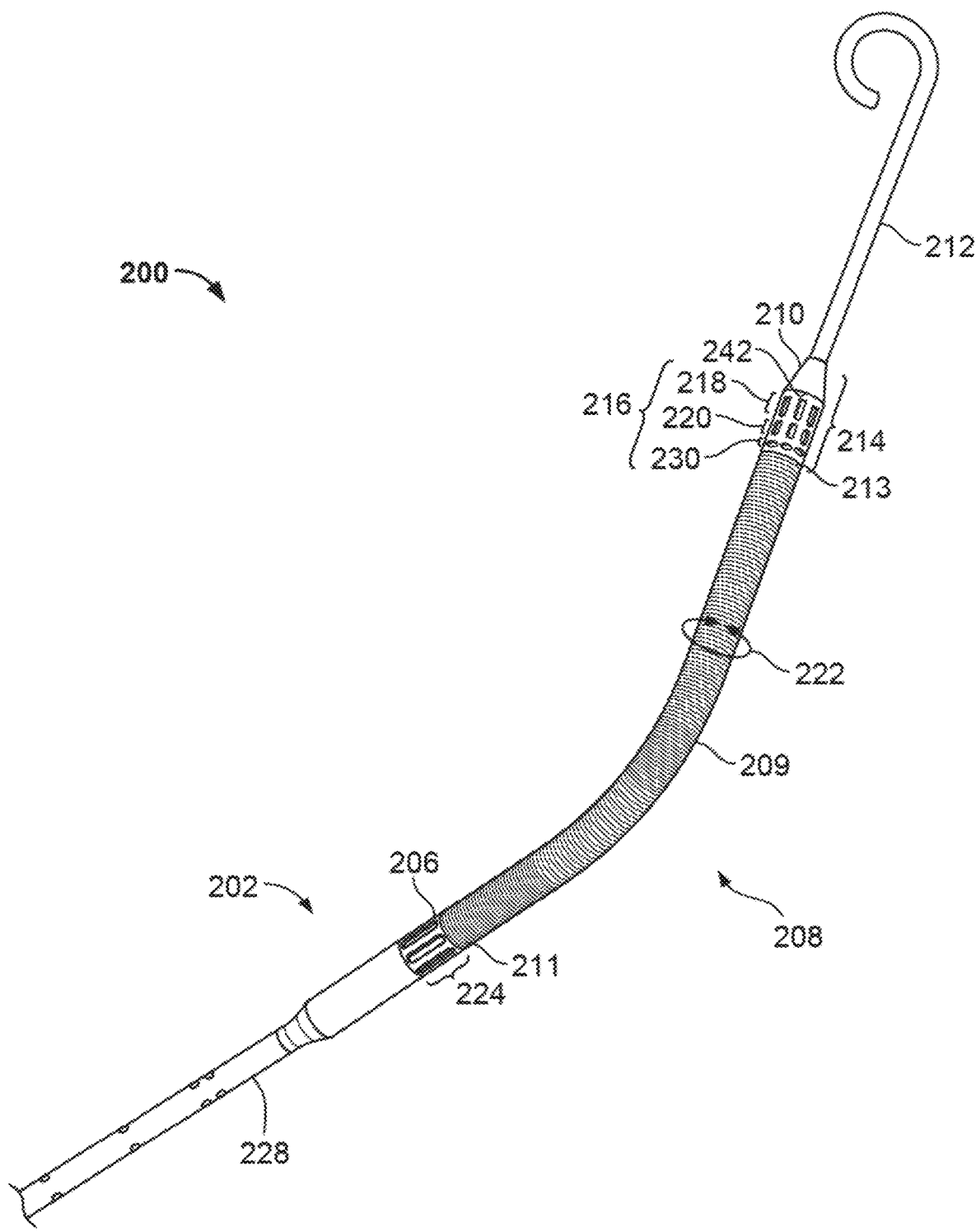
FIG. 2 shows a heart pump assembly including a plurality of apertures at a distal end portion, in accordance with example implementations.

FIG. 2 shows a modified heart pump assembly 200 having a plurality of apertures arranged into rings, according to certain implementations. The heart pump assembly 200 includes a motor housing 202, a cannula assembly 208, a plurality of apertures 216, a plurality of blood exhaust outlets 224, and an atraumatic tip 212. The cannula assembly 208 has a proximal end 206, a cannula body 209, an inflow cage 213, a distal end 210, a distal end portion 214, and a tear drop portion 242. The atraumatic tip 212 is coupled to the cannula assembly 208 at a distal end 210 of the cannula assembly 208 at the tear drop portion 242. The plurality of apertures 216 are arranged in the inflow cage 213 at the distal end portion 214 of the cannula assembly 208. The plurality of apertures 216 each have a smaller area relative to the plurality of apertures 116 shown in FIG. 1, and are arranged into multiple rings. The distal end portion 214 of the cannula assembly 208 includes a first ring 218 of apertures, a second ring 220 of apertures, and a third ring 230 of apertures. The inflow cage 213, including the plurality of apertures 216, is approximately the same length as in the inflow cage 113 of the prior art pump 100, but the plurality of apertures 216 includes more apertures which are smaller than those of the prior art pump 100.

The plurality of smaller apertures 216 arranged in rings 218, 220, and 230 reduces the tendency of the plurality of apertures 216 to suck against the interior of the heart of the patient. In particular, the multiple smaller apertures 216 prevent the heart pump assembly 200 from sucking a valve leaflet into the plurality of apertures 216. This can reduce the risk of occlusion of the apertures 216, thereby allowing the heart pump assembly 200 to provide more assistance to the heart. The apertures 216 may also decrease the risk of damage to structures of the heart which could otherwise be suctioned by the heart pump assembly 200. The heart pump assembly 200 can vary in any number of ways. For example, the embodiment of FIG. 2 and any of the other embodiments herein may exclude a motor housing. Instead, the motor can be configured to be positioned outside of a patient's body and can operatively couple to the rotor via a drive shaft or cable.

Figure 3:
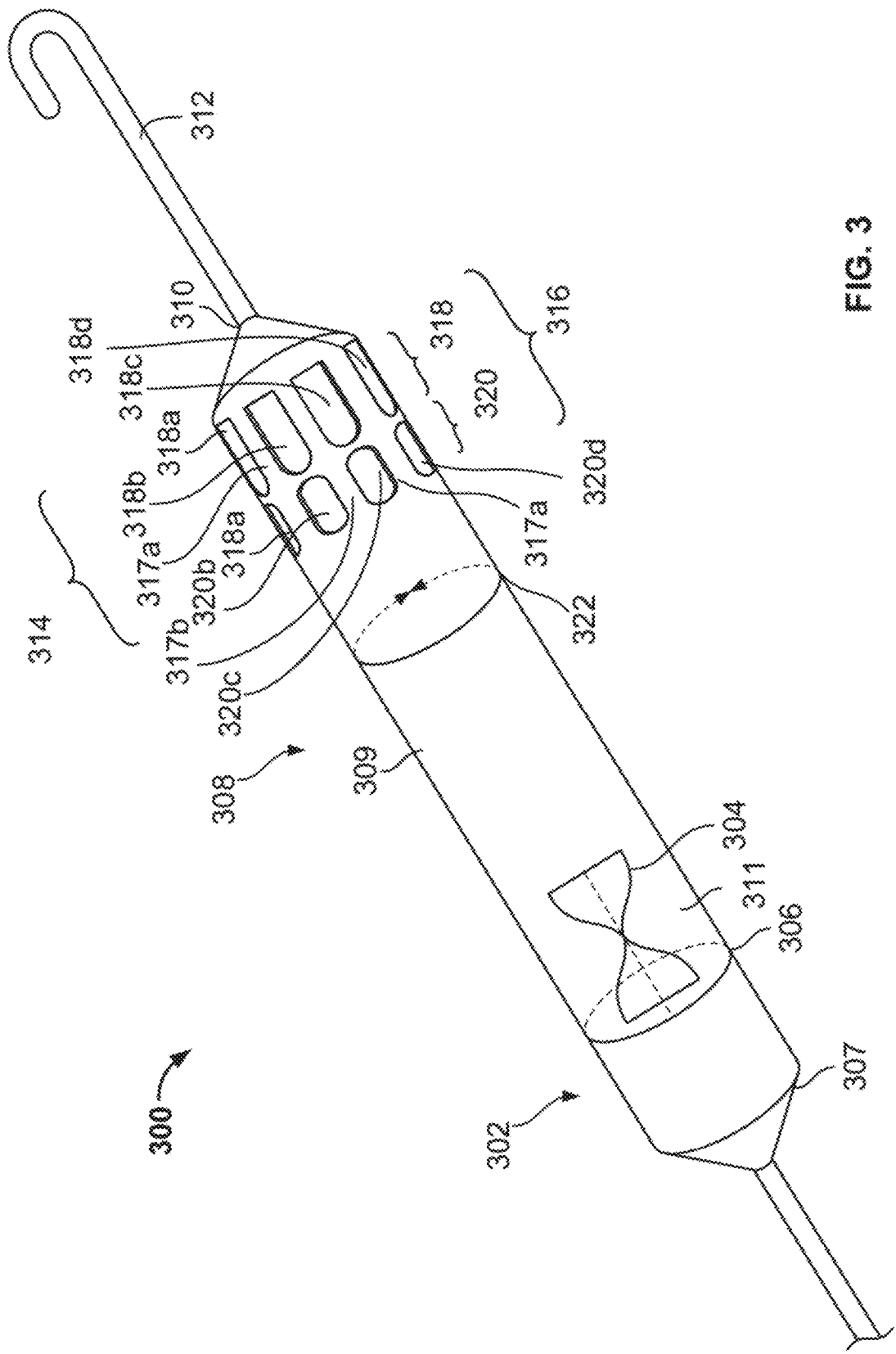
FIG. 3 shows a heart pump assembly including a plurality of apertures arranged in rings at a distal end portion, in accordance with example implementations.

FIG. 3 shows an illustrative view of a heart pump assembly 300, such as heart pump assembly 200 in FIG. 2, including a plurality of apertures 316 at a distal end portion 314 according to some implementations. The heart pump assembly 300 includes a motor housing 302, an impeller blade 304, a cannula assembly 308, a plurality of apertures 316, and an atraumatic tip 312. The motor housing 302 has a distal end 306 and a proximal end 307. The impeller blade 304 is rotatable relative to the cannula assembly 308. The cannula assembly 308 includes a proximal end 311, a distal end 310, a distal end portion 314, a tear drop portion 342 and a cannula body 309 having a circumference 322. The cannula body 309 is coupled to the distal end 306 of the motor housing 302. The plurality of apertures 316 are arranged into a first ring 318 and a second ring 320. The first ring 318 is positioned at a distal end of the distal end portion 314 and the second ring 320 is positioned proximal of the first ring 318. In some implementations, the plurality of apertures 316 are formed in the distal end portion 314 of the cannula assembly 308. In certain implementations, the plurality of apertures 316 are formed in an inflow cage (not shown) which is distinct from, but coupled to, the distal end portion 314 of the cannula assembly 308. The plurality of apertures is separated by a plurality of struts, for example 317a-c. The atraumatic tip 312 is coupled to the distal end 310 of the cannula assembly 308.

The first ring 318 includes apertures 318a-c. The second ring 320 includes apertures 320a-c. Though the first ring 318 and the second ring 320 are shown with three apertures each (318a-c and 320a-c), the plurality of apertures 316 in the first ring 318 and in the second ring 320 can extend around the entire circumference 322 of the cannula body 309. The first ring 318 and the second ring 320 can each include any suitable number of apertures. In some implementations, the number of apertures in a first ring 318 or the second ring 320 is 3, 4, 5, 6, 7, 8, 9, 10 or any other suitable number of apertures. In some implementations, the number of apertures in the first ring 318 is the same as the number of apertures in the second ring 320, though this is not required. In some implementations, there are fewer apertures in the first ring 318 than in the second ring 320. In some implementations, there are more apertures in the first ring 318 than in the second ring 320.

The heart pump assembly 300 pulls blood into the cannula assembly 308 by the rotation of the impeller blade 304. The blood enters the cannula assembly 308 at the plurality of apertures 316 at the distal end portion 314 of the cannula assembly 308. The heart pump assembly 300 may be positioned in the heart in such a way that the mitral valve leaflets are proximate to the plurality of apertures 316, and in some instances, the mitral valve leaflets may be sucked against some of the plurality of apertures 316, temporarily blocking blood from entering at the plurality of apertures 316. Because the plurality of apertures 316 are small in size, the apertures 316 are less likely to allow a valve leaflet to enter the heart pump assembly 300 at an inlet. This keeps the interior of the cannula assembly 308 clear for the passage of blood. Furthermore, the struts 317a-c between the plurality of apertures 316 act as a screen to prevent the suctioning of valve leaflets and other tissues to the plurality of apertures 316. A valve leaflet or other portion of the anatomy that is suctioned against some of the plurality of apertures 316, or into the heart pump assembly 300, decreases the area through which blood can enter the cannula assembly 308, potentially decreasing the flow rate of the blood through the heart pump assembly 300. The plurality of apertures 316 arranged at the distal end portion 314 of the cannula assembly 308 increases the likelihood that some of the plurality of apertures 316 will not be blocked. If a subset of the plurality of apertures 316 are blocked, blood can still enter the heart pump assembly 300 through the remainder of the plurality of apertures 316.

The plurality of apertures 316 are shown having an oblong shape. The plurality of apertures 316 may have any suitable shape to allow blood to enter the cannula assembly. For example, the plurality of apertures 116 can be oblong, oval, square, tear-shaped, round or any other suitable shape. The shape of the apertures 318a-c of the first ring 318 may differ from the shape of the apertures 320a-c of the second ring 320. In some implementations, edges of the plurality of apertures 316 are rounded or chamfered. Rounded apertures, or apertures with rounded edges, may decrease the risk of hemolysis or other damage to the blood as it enters the plurality of apertures 316. As shown, the apertures 318a-c of the first ring 318 each have a greater area relative to each of the apertures 320a-c of the second ring 320. In some implementations, the apertures 318a-c of the first ring 318 each have a smaller area relative to each of the apertures 320a-c of the second ring 320. In certain implementations, each of the apertures 318a-c of the first ring 318 has the same area as each of the apertures 320a-c of the second ring 320.

The atraumatic tip 312 coupled to the distal end 310 of the cannula assembly 308 spaces the plurality of apertures 316 from the inner surface of the heart. This spacing prevents the plurality of apertures 316 from suctioning to the walls of the heart, heart valves (e.g., the mitral valve), or any other anatomical structure in the heart. This can reduce the risk of blockage of the plurality of apertures 316 and may reduce or prevent damage to the heart tissues. The atraumatic tip 312 may be shaped as a flexible extension having a pigtail as shown in FIG. 3. In some implementations, the atraumatic tip 312 is configured as a straight extension or as a ball. In some implementations, the atraumatic tip 312 includes a lumen for the passage of a guidewire through the atraumatic tip 312.

In sum, both the atraumatic tip 312 and the arrangement of apertures 316 help prevent or reduce the risk of a pump inlet being occluded by the heart wall, valve leaflets, or other anatomical structures. The atraumatic tip 312 acts as a mechanical spacer to prevent suction of the apertures against the inner surface of the heart, while the arrangement of apertures 316 and struts 317a-c act as a screen to prevent entry of tissue into the apertures 316. Thus, the atraumatic tip 312 and the arrangement of the apertures 316 together help preserve proper functioning of the heart pump assembly 300.

Figure 4:
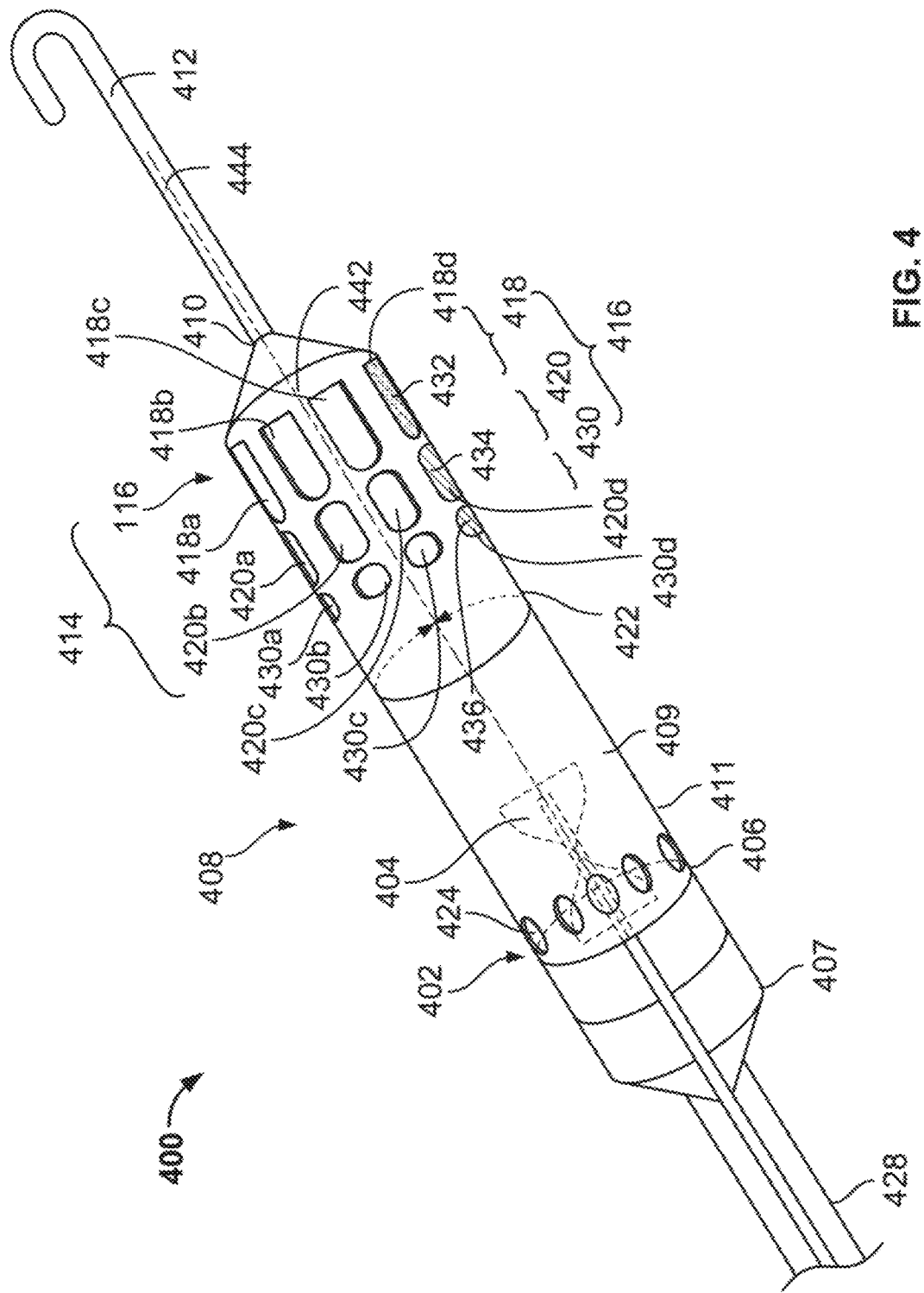
FIG. 4 shows a heart pump assembly including three rings of apertures at a distal end portion, in accordance with example implementations.

FIG. 4 shows an illustrative view of a heart pump assembly 400, such as the heart pump assembly 200 in FIG. 2, including three rings of apertures at a distal end portion 414 of the cannula assembly 408. The heart pump assembly 400 includes a motor housing 402, an impeller blade 404, a catheter 428, a cannula assembly 408, blood exhaust outlets 424, a plurality of apertures 416, and an atraumatic tip 412. The cannula assembly 408 includes a proximal end 411, a distal end 410, a distal end portion 414, a tear drop portion 442, a longitudinal axis 444, and a cannula body 409 having a circumference 422. The motor housing 402 includes the impeller blade 404 which is rotatable relative to the cannula assembly 408. Rotation of the impeller blade 404 creates suction through the cannula assembly 408. Blood enters the cannula assembly 408 at the plurality of apertures 416 disposed in the distal end portion 414 of the cannula assembly 408. The plurality of apertures 416 are arranged about the circumference 422 of the cannula body 409 in a first ring 418 having apertures 418a-d, a second ring 420 having apertures 420a-d, and a third ring 430 having apertures 430a-d. The first ring 418 is proximal to the distal end 410 of the cannula assembly 408. The second ring 420 is proximal of the first ring 418, and the third ring 430 is proximal of the second ring 420. The plurality of apertures 416 are separated by a plurality of struts 217a-c. Attached to the cannula assembly 408 at the tear drop portion 442 at the distal end 410 is the atraumatic tip 412.

Each of the plurality of apertures 416 has a height, a width, and an area. The plurality of apertures 416 can have a variety of sizes. The first ring 418 may have the aperture 418d having a larger area than the aperture 420d of the second ring or the aperture 430d of the third ring 430. The area of the aperture 418d of the first ring 418 may be less than 20 mm$^2$. In some implementations, the area of the aperture 418d of the first ring 218 is 0.5 mm$^2$, 1 mm$^2$, 5 mm$^2$, 10 mm$^2$, 15 mm$^2$, 18 mm$^2$, 20 mm$^2$, 23 mm$^2$, 25 mm$^2$ or any other suitable area. The area of the aperture 420d of the second ring 420 may be less than 12 mm$^2$. In some implementations, the area of the apertures 420d of the second ring 420 may be 0.25 mm$^2$, 0.5 mm$^2$, 1 mm$^2$, 2 mm$^2$, 5 mm$^2$, 10 mm$^2$, 12 mm$^2$, or any other suitable area. The area of the aperture 430d of the third ring 430 may be the same as the area of the aperture 420d of the second ring. The height of the apertures 418b of the first ring 418 as measured along an axis parallel to the longitudinal axis 444 of the cannula assembly 408 may be less than 9 mm. In some implementations, the height of the aperture 418b of the first ring 418 is 0.5 mm, 1 mm, 3 mm, 5 mm, 6 mm, 9 mm, 10 mm, 12 mm, 15 mm or any other suitable height. The height of the aperture 420b of the second ring 420 as measured along an axis parallel to the longitudinal axis 444 of the cannula assembly 408 may be less than 3 mm. In some implementations, the height of the aperture 420b of the second ring 420 is 0.25 mm, 0.5 mm, 1 mm, 1.5 mm, 2 mm, 2.5 mm, 3 mm, 3.5 mm, 4 mm, 5, mm, 6 mm, or any other suitable height. A width of the aperture 420b of the second ring 420 measured transverse to the longitudinal axis 444 may be less than 4 mm. In some implementations, the width of the aperture 420b of the second ring 420 is 0.5 mm, 1 mm, 1.5 mm, 2 mm, 2.5 mm, 3 mm, 3.5 mm, 4 mm, 5, mm, 6 mm, 8 mm, or any other suitable width. In some implementations, a height and the width of aperture 430b is the same as the height and the width of aperture 420b.

The plurality of apertures 416 prevents the heart pump assembly 400 from failing due to the suction of a valve leaflet against a portion of the plurality of apertures 416. The plurality of apertures 416 arranged in rings 418, 420, and 430, reduces the tendency of the plurality of apertures 416 to suck heart structures against the inlets of the heart pump assembly 400. The multiple apertures 416, along with the struts 417a-c, prevent the heart pump assembly 400 from sucking a valve leaflet into the plurality of apertures 416, thereby reducing risk of blocking the apertures 416 and allowing the heart pump assembly 400 to continue to provide assistance to the heart. Furthermore, the plurality of apertures 416 provide redundant inflow inlets for blood to enter even if one or more of the plurality of apertures 416 is blocked by a valve leaflet or other tissue.

In some implementations, a large portion of blood that enters the cannula assembly 408 enters through the most proximal of the plurality of apertures 416, for example through the apertures 430a-c of the third ring 430. When one or more of the plurality of apertures 416 in the third ring 430 is blocked, a larger amount of blood may enter at the plurality of apertures 416 in the second ring 420 or the first ring 418. Additional apertures provide additional inlets through which blood can enter the heart pump assembly. Additionally, the struts 417a-c that define the plurality of apertures 416 can act as a screen to prevent the suction of tissue against, or into, the heart pump assembly 400.

Figure 5:
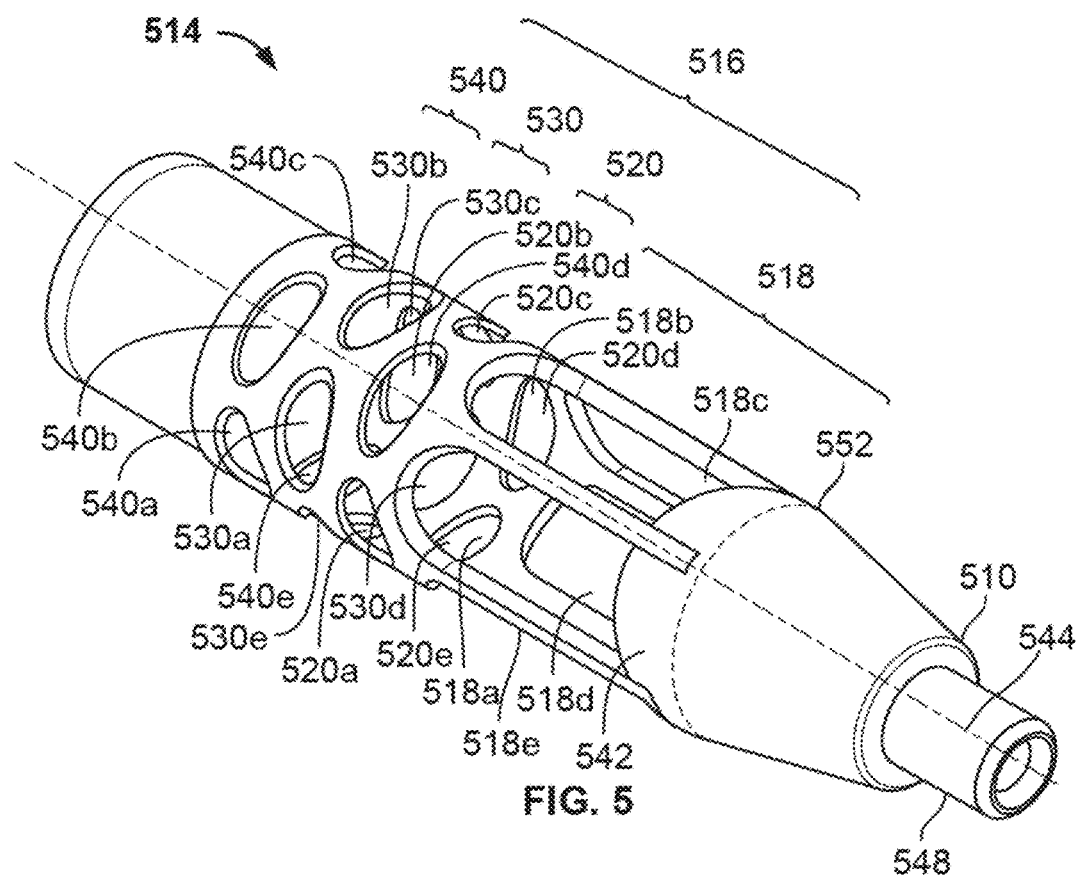
FIG. 5 shows a perspective view of a distal end portion of a heart pump assembly having four rings of apertures, in accordance with example implementations.
Figure 6:
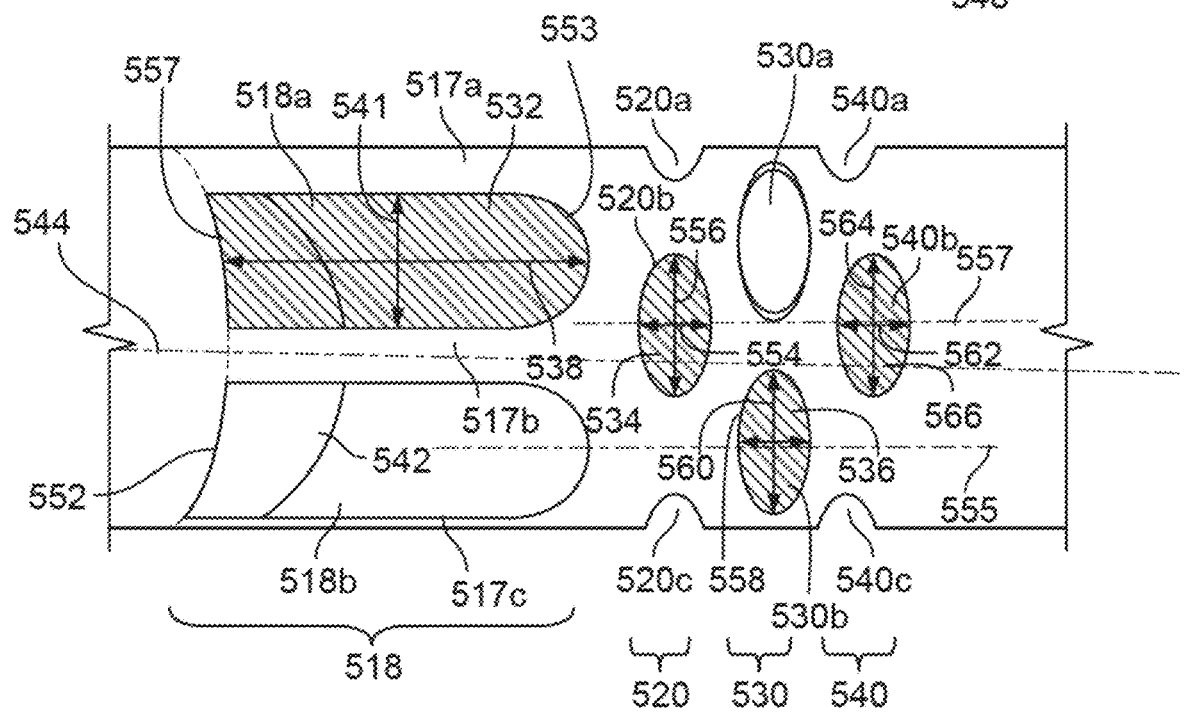
FIG. 6 shows a front view of a distal end portion of a heart pump assembly having four rings of apertures, in accordance with example implementations.

While FIG. 4 shows a heart pump assembly 400 having a plurality of apertures arranged in three rings, in some implementations there may be additional rings of apertures. For example, FIG. 5 shows a perspective view of a distal end portion 514 of a cannula assembly having four rings of apertures, and FIG. 6 shows a front view of the distal end portion 514 of the cannula assembly of FIG. 5. The distal end portion 514 includes a distal end 510, an atraumatic tip connector 548, a tear drop portion 542, a longitudinal axis 544, and a plurality of apertures 516 arranged in a first ring 518, a second ring 520, a third ring 530, and a fourth ring 540. The plurality of apertures 516 in the first ring 518 include apertures 518a-e oriented radially around a circumference of the distal end portion 514. The second ring 520 of apertures 520a-e, the third ring 530 of apertures 530a-e, and the fourth ring 540 of apertures 540a-e are radially oriented around a circumference of the distal end portion 514.

The first ring 518 of apertures 518a-e has the largest height of the four rings of apertures. The first ring 518 of apertures 518a-e has a distal edge 551 of each aperture which is defined by a portion 552 of the tear drop portion 542. The tear drop portion 542 may be manufactured separately from the rest of the cannula assembly in which the rest of the plurality of apertures 516 are disposed, and may be joined to the cannula assembly (not shown) as part of the manufacturing process. As a result, the first ring 518 of apertures 518a-c may be formed in the cannula assembly (or in the inflow cage, not shown) during the manufacture process as initially only having defined three sides, with a fourth, distal side left open. The fourth, distal edge 551 of each aperture 518a-e is then defined by a portion 552 of the tear drop portion 542 when it is joined to the cannula assembly. The proximal edge 553 of the apertures 518a-e is rounded, giving the apertures 518a-e an oblong shape.

The apertures 520a-e of the second ring 520 are rotationally offset from the apertures 518a-e of the first ring, such that a line 555 drawn through the center of aperture 518b parallel to the longitudinal axis 544 of the distal end portion 514 does not pass through a center of any of the apertures 520a-e of the second ring 520. In some implementations, the line 555 may pass through a portion of one of the apertures 520a-e, but not the center of apertures 520a-e. The apertures 530a-e are rotationally aligned with the apertures 518a-e, such that the line 555 passes through a center of the one of apertures 518a-e and a center of one of the apertures 530a-e. In particular, the line 555 passes through the center of aperture 518b and the center of aperture 530b. The line 555 does not pass through the center of any of the apertures 540a-e of the fourth ring 540, as the apertures 540a-e are rotationally offset from the apertures 518a-e and the apertures 530a-e. The apertures 520a-e of the second ring 520 are rotationally aligned with the apertures 540a-e of the fourth ring 540 such that the line 557 parallel to the longitudinal axis 544 of the distal end portion 514 passes through a center of aperture 520b and 540b. In some implementations, different rings of apertures may be rotationally aligned or offset. For example, in some implementations the apertures 518a-e and 520a-e of the first ring 518 and second ring 520, respectively, may be rotationally aligned, while the apertures 530a-e of the third ring 530 and apertures 540a-e of the fourth ring 540 are not rotationally aligned with the first ring 518 and the second ring 520. In some implementations, the apertures 518a-e and the apertures 530a-e are aligned, and the apertures 520a-e and the apertures 540a-e are rotationally offset from the first ring 518 and the third ring 530. In some implementations, the second ring 520 and fourth ring 540 are rotationally offset from first ring 518 by different amounts such that a line 557 drawn through an aperture 520b of the second ring 520 does not pass through a center of any aperture 540a-e of the fourth ring 540.

Each of the apertures 518a-e, 520a-e, 530a-e, and 540a-e of the plurality of apertures 516 has an associated height measured parallel to the longitudinal axis 544, a width measured transverse to the longitudinal axis 544, and an area. For example, aperture 518a has a height 538 and a width 541. Aperture 518a also has an area 532 through which blood may pass. The aperture 520b of the second ring 520 has a height 554, a width 556 and an area 534. The aperture 530b of the third ring 530 has a height 558, a width 560 and an area 536. The aperture 540b of the fourth ring 540 has a height 562, a width 564 and an area 566. In some implementations, the measurements including one or more of the height, the width and the area of the apertures in a particular ring are common to all the apertures in that ring, however this is not required. In some implementations, the measurements, including one or more of the height, width, and area, vary amongst the apertures in a particular ring. In some implementations, the apertures 520a-e in the second ring 520, the apertures 530a-e in the third ring 530, and the apertures 540a-e in the fourth ring 540, have the same measurements including one or more of the height, width and area. In some implementations, one or more of the height, width or area of the apertures vary between the apertures 520a-e in the second ring 520, the apertures 530a-e in the third ring 530, and the apertures 540a-e in the fourth ring 540. In some implementations, the combined areas of the apertures 518a-e of the first ring 518, the apertures 520a-e in the second ring 520, the apertures 530a-e in the third ring 530, and the apertures 540a-e in the fourth ring 540 is equal to or greater than a cross-sectional area of the cannula assembly.

Despite the apertures 518a-e of the first ring 518 having a larger area 532 than the apertures 520a-e in the second ring 520, the apertures 530a-e in the third ring 530, and the apertures 540a-e in the fourth ring 540, blood flows predominantly through the most proximal apertures of the plurality of apertures 516 due to the smaller pressure drop at these apertures. If all or a portion of the apertures 540a-e of the fourth ring 540 are blocked by a valve leaflet, the blood may still flow through the rest of the apertures. The smaller areas of the apertures 520a-e in the second ring 520, the apertures 530a-e in the third ring 530, and the apertures 540a-e in the fourth ring 540, and the struts 517a-c between the inlets decreases the likelihood that the additional inlets will be blocked by a valve leaflet.

Figure 7:
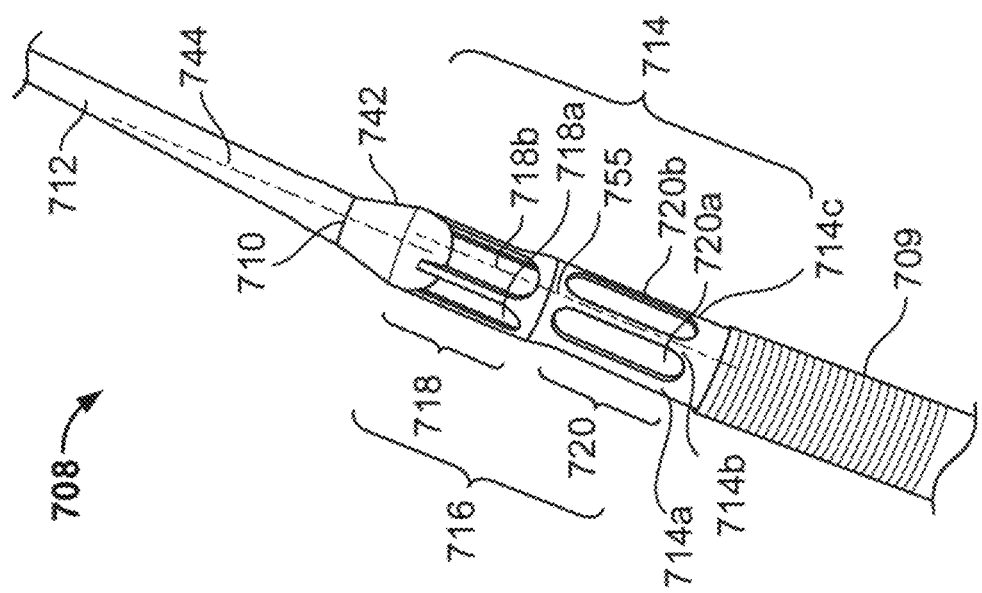
FIG. 7 shows a perspective view of a distal end portion of a heart pump assembly having two rotationally offset rings of apertures, in accordance with example implementations.

FIG. 7 shows a front view of a distal end portion 714 of a cannula assembly 708 having a plurality of apertures 716 which are arranged in two rotationally offset rings. The cannula assembly 708 includes a cannula body 709, a distal end portion 714, a distal end 710, an atraumatic tip 712, a tear drop portion 742, a longitudinal axis 744, a plurality of struts 717a-c, and a plurality of apertures 716. The plurality of apertures 716 is arranged in a first ring 718 of apertures 718a-b, and a second ring 720 of apertures 720a-b. The plurality of apertures 716 in the cannula assembly 708 are arranged such that the first ring 718 of apertures 718a-b is rotationally offset from the second ring 720 of apertures 720a-b. A line 755 drawn parallel to the longitudinal axis 744 of the cannula assembly 708 through a center of aperture 718a of the first ring 718 does not pass through a center of any of apertures 720a-b of the second ring 720. The line 755 instead passes through the strut 717b dividing aperture 720a and aperture 720b of the second ring 720. Rotationally offset apertures may prevent a valve leaflet from completely blocking more than one of the apertures. For example, if a valve leaflet is suctioned to the cannula assembly 708 such that it covers aperture 718a of the first ring 718, the rotational offset of the second ring 720 of apertures 720a-b may prevent the valve leaflet from blocking all of an additional aperture 720a or 720b of the second ring 720.

Figure 8:
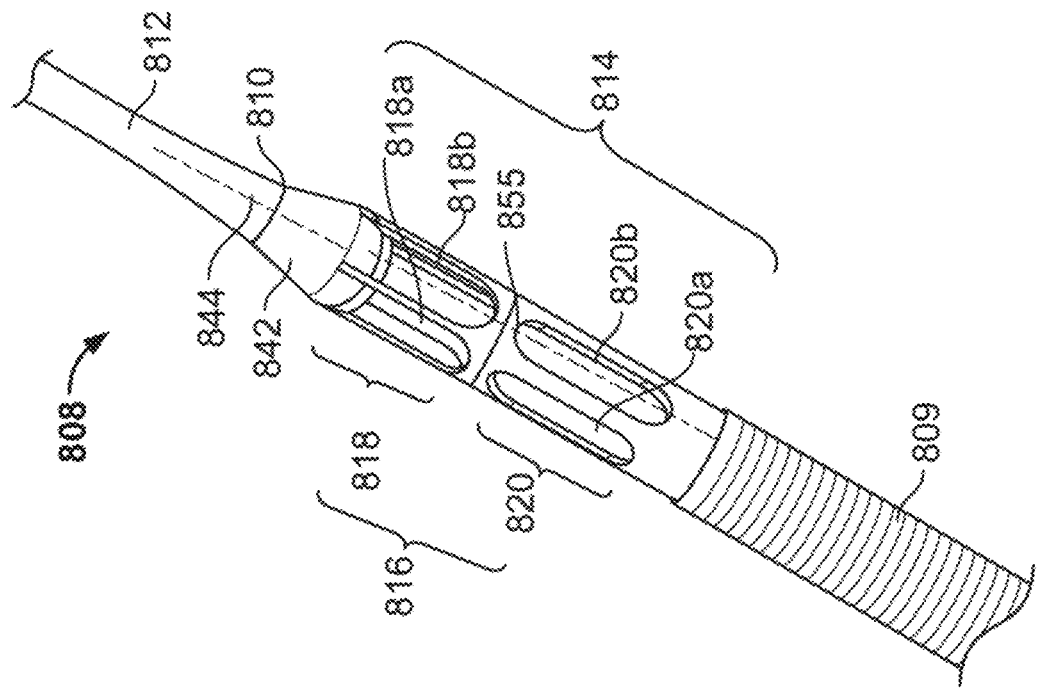
FIG. 8 shows a perspective view of a distal end portion of a heart pump assembly having two rotationally aligned apertures, in accordance with example implementations.
Figure 9:
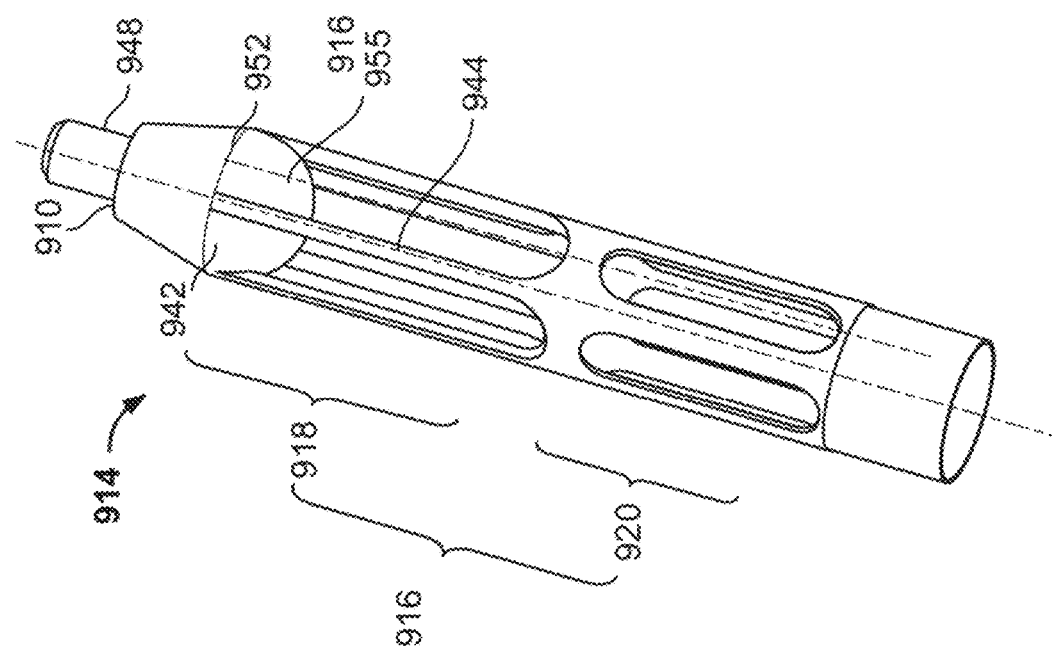
FIG. 9 shows a perspective view of a distal end portion of a heart pump assembly having a plurality of rotationally aligned apertures, in accordance with example implementations.

While FIGS. 5, 6 and 7 show a distal end portion of a cannula assembly (for example, distal end portion 514 of FIG. 5 or distal end portion 714 of FIG. 7) with a plurality of rotationally offset apertures (for example, plurality of apertures 516 of FIG. 5 or plurality of apertures 716 of FIG. 7), FIG. 8 shows a perspective view of a distal end portion 814 of a cannula assembly 808 in which the plurality of apertures 816 are rotationally aligned with one another. FIG. 9 shows an alternative perspective view of the distal end portion 914 with a plurality of rotationally aligned apertures 916. The cannula assembly 908 includes a cannula body 909, a distal end portion 914, a distal end 910, an atraumatic tip 912, a tear drop portion 942, an atraumatic tip connector 948, a longitudinal axis 944, and a plurality of apertures 916. The plurality of apertures 916 are arranged in a first ring 918 of apertures 918a-d, and a second ring 920 of apertures 920*a-d*. The plurality of apertures 916 in cannula assembly 908 are arranged such that the first ring 918 of apertures 918*a-d* is rotationally aligned with the second ring 920 of apertures 920*a-d*. A line 955 drawn parallel to the longitudinal axis 944 of the cannula assembly 908 through a center of aperture 918*b* of the first ring 918 also passes through a center of apertures 920*b* of the second ring 920. Apertures 918*a-d* and apertures 920*a-d* are shown with a larger height than width such that the area of each aperture 918*a-d* and 920*a-d* is defined by an oval shape through which blood may enter the cannula assembly 908. Rotationally aligned apertures may be simpler to machine in a cannula assembly 908 than offset apertures.

Figure 10:
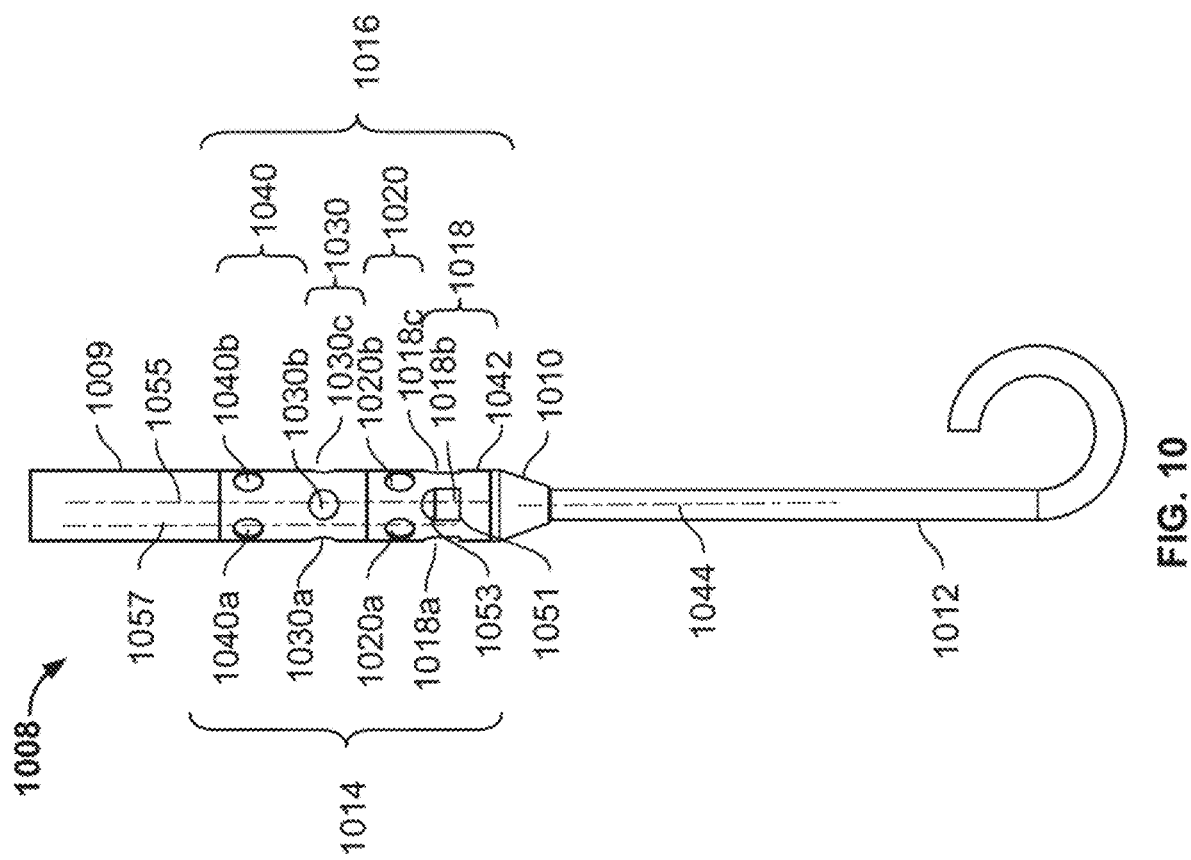
FIG. 10 shows a front view of a distal end portion of a heart pump assembly having a plurality of round apertures, in accordance with example implementations.

FIG. 10 shows a front view of a distal end portion 1014 of a cannula assembly 1008 having a plurality of round apertures 1016, which are rotationally offset from each other. The cannula assembly 1008 of FIG. 10 includes a distal end 1010, distal end portion 1014, an atraumatic tip connector 1048, a tear drop portion 1042, a longitudinal axis 1044, an atraumatic tip 1012, and a plurality of apertures 1016. The plurality of apertures 1016 are disposed in a first ring 1018 of apertures 1018*a-c*, a second ring 1020 of apertures 1020*a-b*, a third ring 1030 of apertures 1030*a-c*, and a fourth ring 1040 of apertures 1040*a-b*. The apertures 1018*a-c* of the first ring 1018 are oblong in shape. In particular, the first ring 1018 of apertures 1018*a-c* are rounded on a proximal edge 1053 and have a distal edge 1051 defined by a portion of the tear drop portion 1042. The apertures 1020*a-b* in the second ring 1020, the apertures 1030*a-c* in the third ring 1030, and the apertures 1040*a-b* in the fourth ring 1040 are circular. The apertures 1018*a-c* in the first ring 1018 and the apertures 1030*a-c* in the third ring 1030 are rotationally aligned such that the line 1055 through a center of aperture 1018*b* passes through a center of the aperture 1030*b*. The apertures 1020*a-b* in the second ring 1020 and the apertures 1040*a-b* in the fourth ring 1040 are rotationally offset from the apertures 1018*a-c* and the apertures 1030*a-c*, but are rotationally aligned with each other such that a line 1057 through a center of the aperture 1020 parallel to the longitudinal axis 1044 of the cannula 1008 passes through a center of the aperture 1040*a*. The plurality of apertures 1016 with circular shapes which are arranged in rings about the cannula assembly 1008 such that the apertures of each ring are rotationally offset from the apertures of the ring directly above or below it may decrease the likelihood that a valve leaflet will block multiple apertures.

Figure 11:
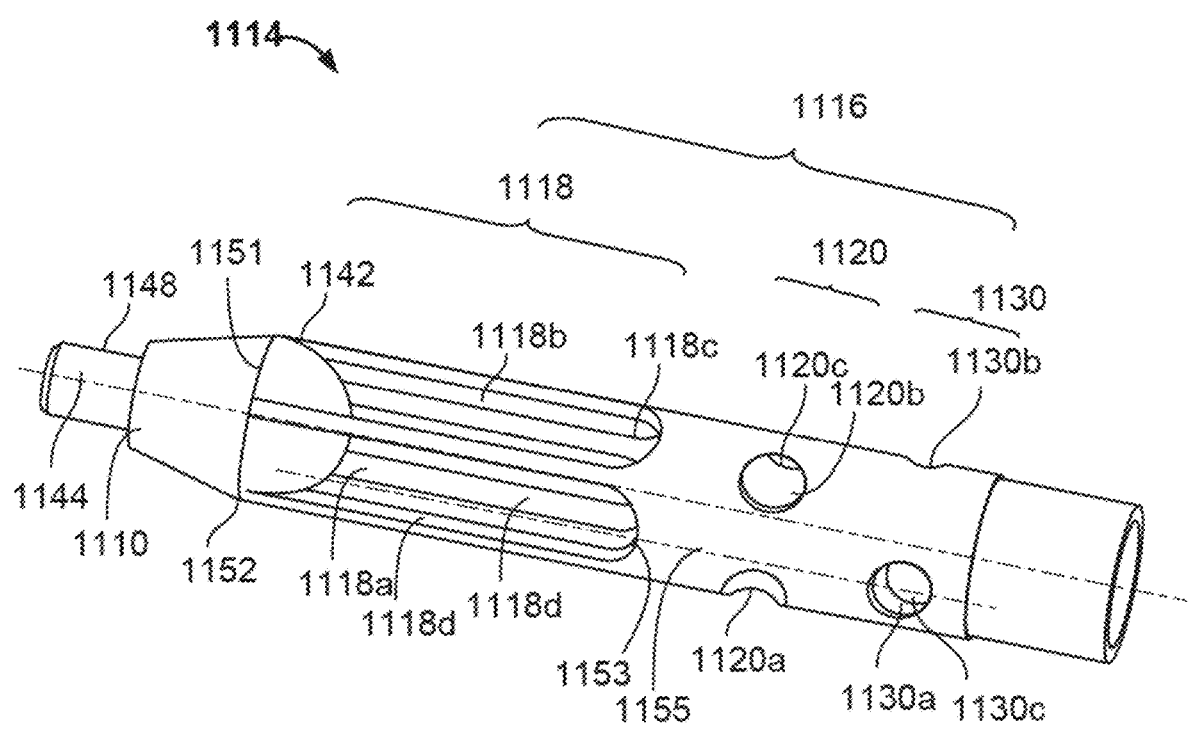
FIG. 11 shows a perspective view of a distal end portion of a heart pump assembly having an oblong distal aperture and a plurality of round apertures, in accordance with example implementations.

While FIG. 10 shows a distal end portion 1014 of a cannula assembly 1008 having a first ring of apertures and three additional rings of round apertures, FIG. 11 shows a distal end portion 1114 of a cannula assembly having a first ring of apertures and only two additional rings of round apertures. The distal end portion 1114 of FIG. 11 includes a distal end 1110, an atraumatic tip connector 1148, a tear drop portion 1142, a longitudinal axis 1144, and a plurality of apertures 1116. The plurality of apertures 1116 are disposed in a first ring 1118 of apertures 1118*a-d*, a second ring 1120 of apertures 1120*a-c*, and a third ring 1130 of apertures 1130*a-c*. The apertures 1118*a-e* of the first ring 1118 are oblong in shape and are defined on a distal edge 1151 by a portion 1152 of the tear drop portion 1142. A proximal edge 1153 of the apertures 1118*a-e* is rounded. The apertures 1120*a-c* in the second ring 1120 and the apertures 1130*a-c* in the third ring 1130 are circular. Like the plurality of apertures 1116 in FIG. 10, the rings of the plurality of apertures 1116 are rotationally offset. For example, the apertures 1118*a-e* in the first ring 1118 and the apertures 1130*a-c* in the third ring 1130 are rotationally aligned such that the line 1155 through a center of the aperture 1118*b* passes through a center of the aperture 1130*a*.

Figure 12:
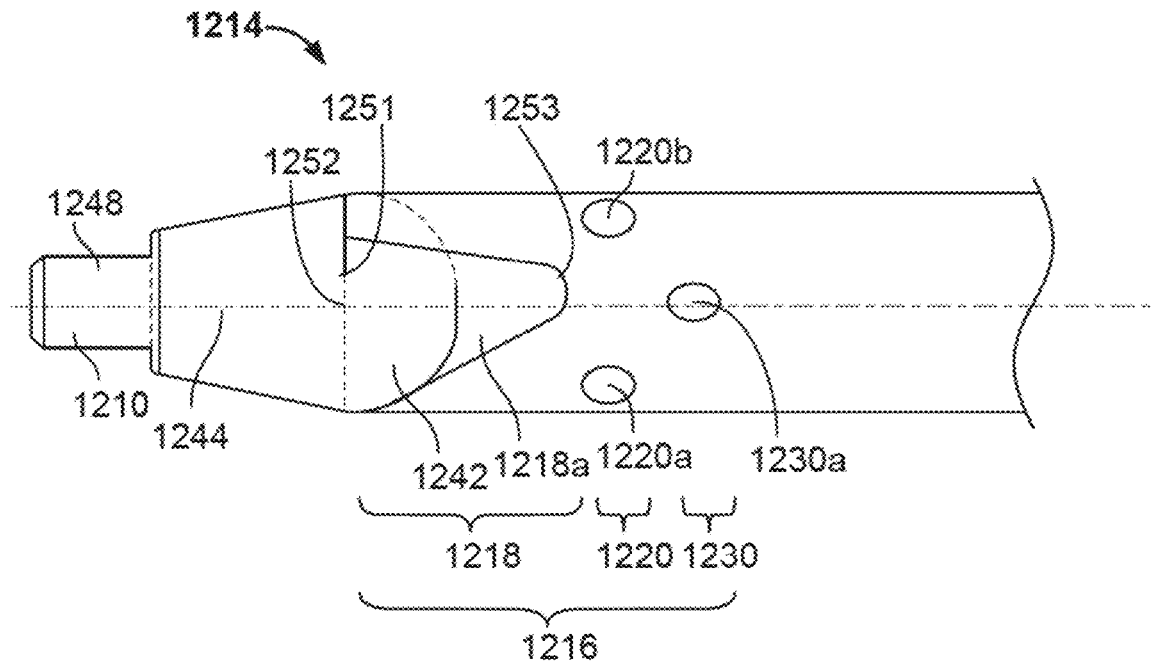
FIG. 12 shows a front view of a distal end portion of a heart pump assembly having a distal tear-shaped aperture and a plurality of round apertures, in accordance with example implementations.

While FIGS. 10 and 11 show distal end portions having a plurality of circular an oblong apertures, FIG. 12 shows a front view of a distal end portion 1214 of a cannula assembly having a plurality of apertures 1216, with a first ring 1218 having apertures 1218*a* with a tear drop shape, while apertures in additional rings are circular. The distal end portion 1214 includes a distal end 1210, an atraumatic tip connector 1248, a tear drop portion 1242, a longitudinal axis 1244, and a plurality of apertures 1216. The plurality of apertures 1216 are disposed in a first ring 1218 of aperture 1218*a*, a second ring 1220 of apertures 1220*a-b*, and a third ring 1230 of aperture 1230*a*. Though a single aperture 1218*a* and 1230*a* are visible in FIG. 12, there may be multiple apertures in each ring 1218, 1220, and 1230 disposed radially about the circumference of the distal end 1214 of the cannula assembly. The apertures 1218*c* in the first ring 1218 are tear-shaped such that a distal edge 1251 defined by a portion 1252 of the tear drop portion 1242 of the atraumatic tip connector 1248 is rounded and a proximal edge 1253 is pointed in a direction of blood flow through the cannula. The second ring 1220 of apertures 1220*a-b*, and the third ring 1230 of aperture 1230*a* are circular. In some implementations, one or both of the second ring 1220 of apertures 1220*a-b*, and the third ring 1230 of aperture 1230*a* are rotationally aligned with the first ring 1218 of apertures 1218*a*.

Figure 13:
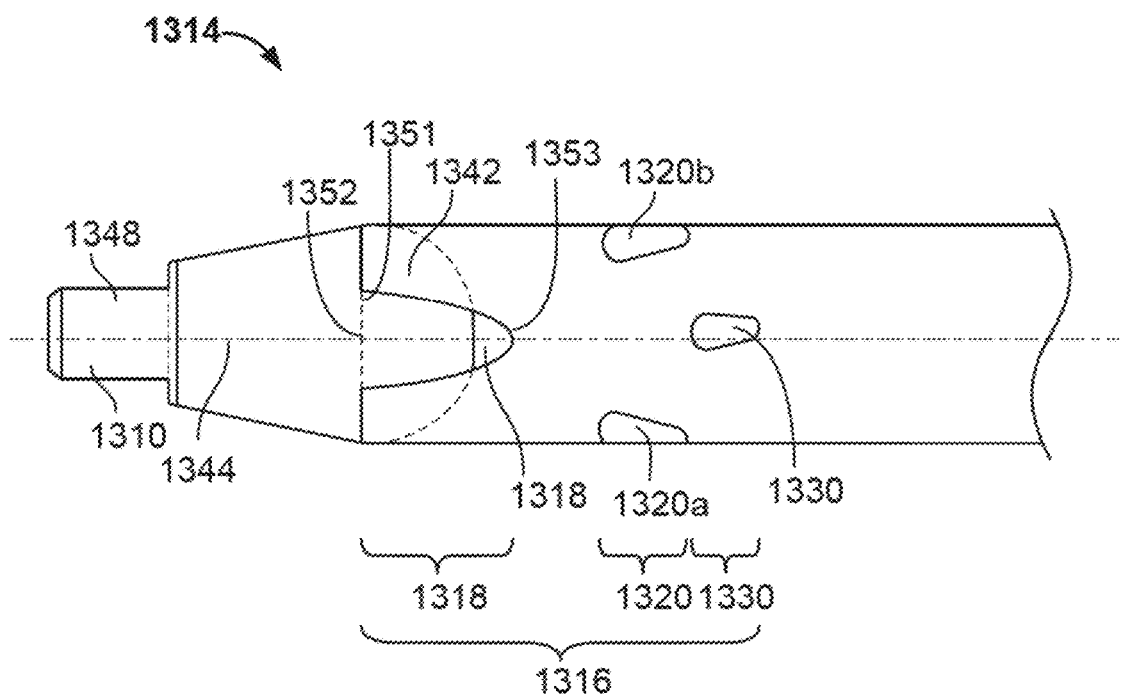
FIG. 13 shows front view of a distal end portion of a heart pump assembly having a distal tear-shaped aperture and a plurality of tear-shaped apertures arranged in rings, in accordance with example implementations.

While FIG. 12 shows a first ring 1218 of tear-shaped apertures with apertures of other rings being circular, in some implementations all of the apertures are tear-shaped. For example, FIG. 13 shows a front view of a distal end portion 1314 having tear-shaped apertures in the first ring 1318 and a plurality of tear-shaped apertures arranged in a second ring 1320 and third ring 1330. The distal end portion 1314 includes a distal end 1310, an atraumatic tip connector 1348, a tear drop portion 1342, a longitudinal axis 1344, and a plurality of apertures 1316 disposed in a first ring 1318 of aperture 1318*a*, a second ring 1320 of apertures 1320*a-b*, and a third ring 1330 of aperture 1330*a*. As in FIG. 11, though a single aperture 1218*a* and 1230*a* are visible in the first ring 1218 and the third ring 1230 in FIG. 12, each ring may include a plurality of apertures disposed about the distal end portion 1214 of the cannula assembly. Similarly to the first ring 1218 of aperture 1218*a* of FIG. 12, the aperture 1318*a* in the first ring is tear-shaped with a rounded distal edge 1351 defined by the tear drop portion 1342 of the atraumatic tip connector 1348 and a proximal edge 1353 that is pointed along the longitudinal axis 1344. The apertures 1320*a-b* in the second ring 1320 and the apertures 1330*a-c* in the third ring 1330 are also tear-shaped, with each aperture having a rounded distal end and a pointed proximal end. The larger opening at a distal end tapering to the pointed opening at a proximal end may facilitate blood flow through the apertures and limit stagnation of the blood as it flows into the plurality of apertures 1316.

Figure 14:
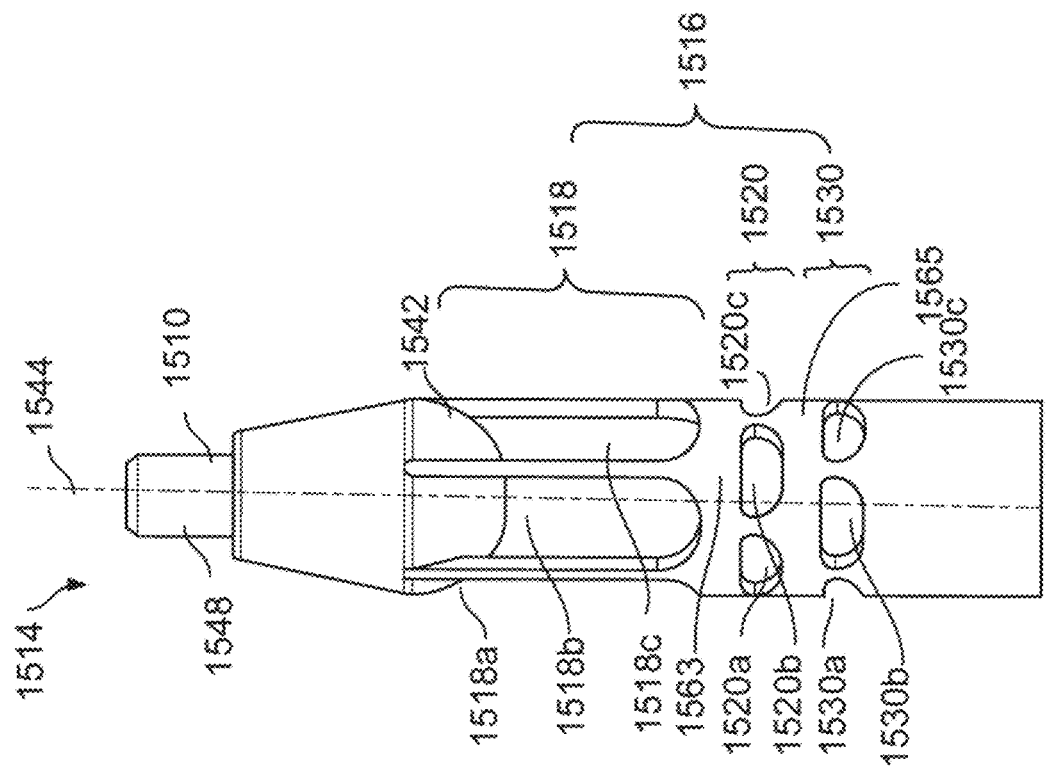
FIG. 14 shows a front view of a distal end portion of a heart pump assembly having an arrangement of apertures positioned in closely spaced rings, in accordance with example implementations.

Variations in the number and size of the apertures in the distal end portion can alter the flow distribution of blood into the cannula. FIGS. 14-23 show further arrangements of apertures in a distal end portion of a cannula. All arrangements in FIGS. 14-23 show the plurality of apertures disposed on a similar portion of the distal end portion of the cannula, but the apertures vary in the shape, positioning, and relative size. FIG. 14 shows a front view of a distal end portion 1414 of a heart pump assembly having a plurality of apertures 1416 arranged into three rings of apertures according to certain implementations. The distal end portion 1414 includes a distal end 1410, an atraumatic tip connector 1448, a tear drop portion 1442, a longitudinal axis 1444, a plurality of apertures 1416, a first circumferential strut 1463 and a second circumferential strut 1465. The circumferential struts 1463 and 1465 run about a circumference of the distal end portion 1414 and divide the plurality of apertures 1416 into rings of apertures. The plurality of apertures 1416 are disposed in a first ring 1418 of apertures 1418a-c, a second ring 1420 of apertures 1420a-c, and a third ring 1430 of apertures 1430a-c. The first circumferential strut 1463 divides the first ring 1418 from the second ring 1420. The second circumferential strut 1465 divides the second ring 1420 from the third ring 1430. The apertures 1418a-c are defined on one side by the tear drop portion 1442. The apertures 1418a-c of the first ring 1418 are oblong in shape, each having a height that is larger than a width. The apertures 1420a-c of the second ring 1420 and apertures 1430a-c of the third ring 1430 are oblong, each having a width that is larger than a height. Additionally, apertures 1420a-c of the second ring 1420 and apertures 1430a-c of the third ring 1430 have a proximal edge which is rounded and a distal edge which is straight.

Figure 15:
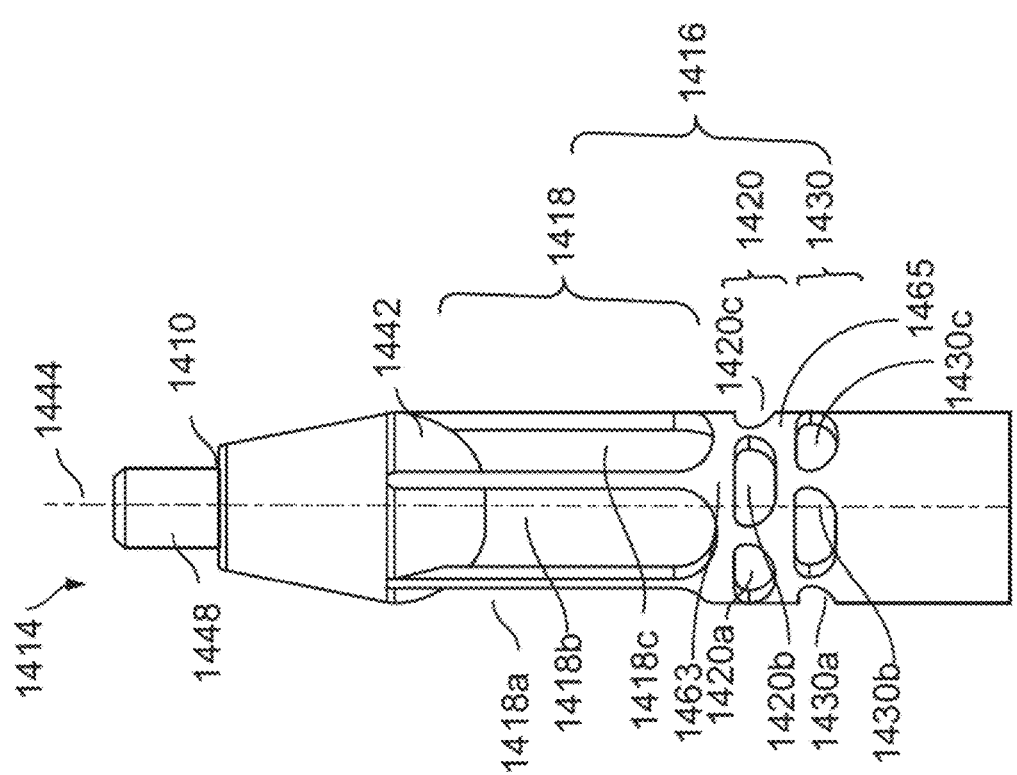
FIG. 15 shows a front view of a distal end portion of a heart pump assembly having an alternative arrangement of apertures positioned in moderately spaced rings, in accordance with example implementations.

FIG. 15 shows a front view of a distal end portion 1514 of a cannula assembly according to certain implementations. The distal end portion 1514 includes a distal end 1510, an atraumatic tip connector 1548, a tear drop portion 1542, a longitudinal axis 1544, a plurality of apertures 1516, a first circumferential strut 1563 and a second circumferential strut 1565. The circumferential struts 1563 and 1565 run about a circumference of the distal end portion 1514 and divide the plurality of apertures 1516 into rings of apertures. The plurality of apertures 1516 are arranged into three rings of apertures, a first ring 1518 of apertures 1518a-c, a second ring 1520 of apertures 1520a-c, and a third ring 1530 of apertures 1530a-c. The first circumferential strut 1563 divides the first ring 1518 from the second ring 1520. The second circumferential strut 1565 divides the second ring 1520 from the third ring 1530. The apertures 1518a-c of the first ring 1518 are defined on one side by the tear drop portion 1542 and have a lesser height along the longitudinal axis 1544 than the apertures 1418a-c of the first ring 1418 in FIG. 14. The size and shape of apertures 1520a-c and apertures 1530a-c are the same as in FIG. 14. Additionally, the first circumferential strut 1563 between the first ring 1518 and second ring 1520 has a larger height in the direction of the longitudinal axis 1544 than the first circumferential strut 1463 dividing the first ring 1418 and second ring 1420 in FIG. 14. This may provide additional area which is non-sucking that can prevent suctioning of the valve leaflets to the cannula assembly according to certain implementations.

Figure 16:
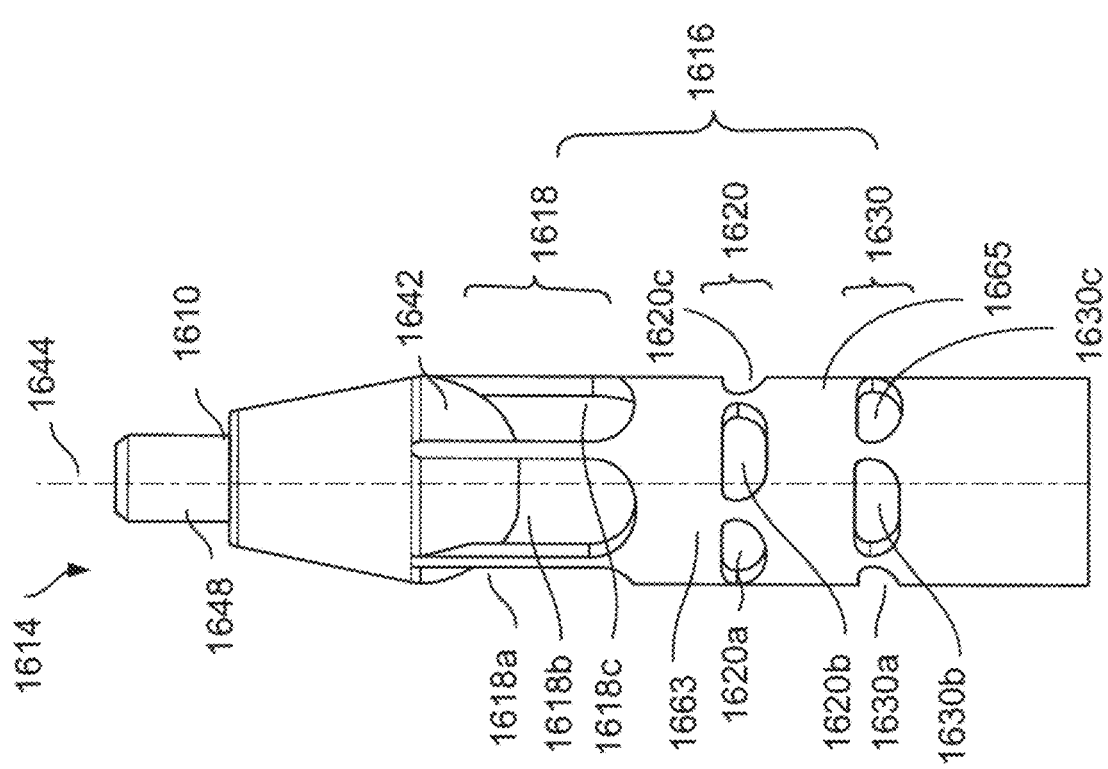
FIG. 16 shows a front view of a distal end portion of a heart pump assembly having an alternative arrangement of apertures positioned in widely spaced rings, in accordance with example implementations.

FIG. 16 shows a front view of a distal end portion 1614 according to certain implementations. The distal end portion 1614 includes a distal end 1610, an atraumatic tip connector 1648, a tear drop portion 1642, a longitudinal axis 1644, a plurality of apertures 1616, and at a first circumferential strut 1663 and a second circumferential strut 1665. The circumferential struts 1663 and 1665 run about a circumference of the distal end portion 1614 and divide the plurality of apertures 1616 into rings of apertures. The plurality of apertures 1616 are arranged into three rings of apertures, a first ring 1618 of apertures 1618a-c, a second ring 1620 of apertures 1620a-c, and a third ring 1630 of apertures 1630a-c. The first circumferential strut 1663 divides the first ring 1618 from the second ring 1620. The second circumferential strut 1665 divides the second ring 1620 from the third ring 1630. The apertures 1618a-c of the first ring 1618 are defined on one side by the tear drop portion 1642. A height of the apertures 1618a-c of the first ring 1618 which is less than the height of the apertures 1518a-c of the first ring 1518 in FIG. 15. The size and shape of apertures 1620a-c and apertures 1630a-c are the same as in FIGS. 14 and 15, but the height of the apertures 1618a-c of the first ring 1618 is less than the height of the corresponding apertures in FIGS. 14 and 15. The first circumferential strut 1663 dividing the first ring 1618 from the second ring 1620 is additionally greater in height along the longitudinal axis 1644 in the arrangement of FIG. 16 than in the corresponding circumferential struts 1463 and 1563 in FIG. 14 or 15.

Figure 17:
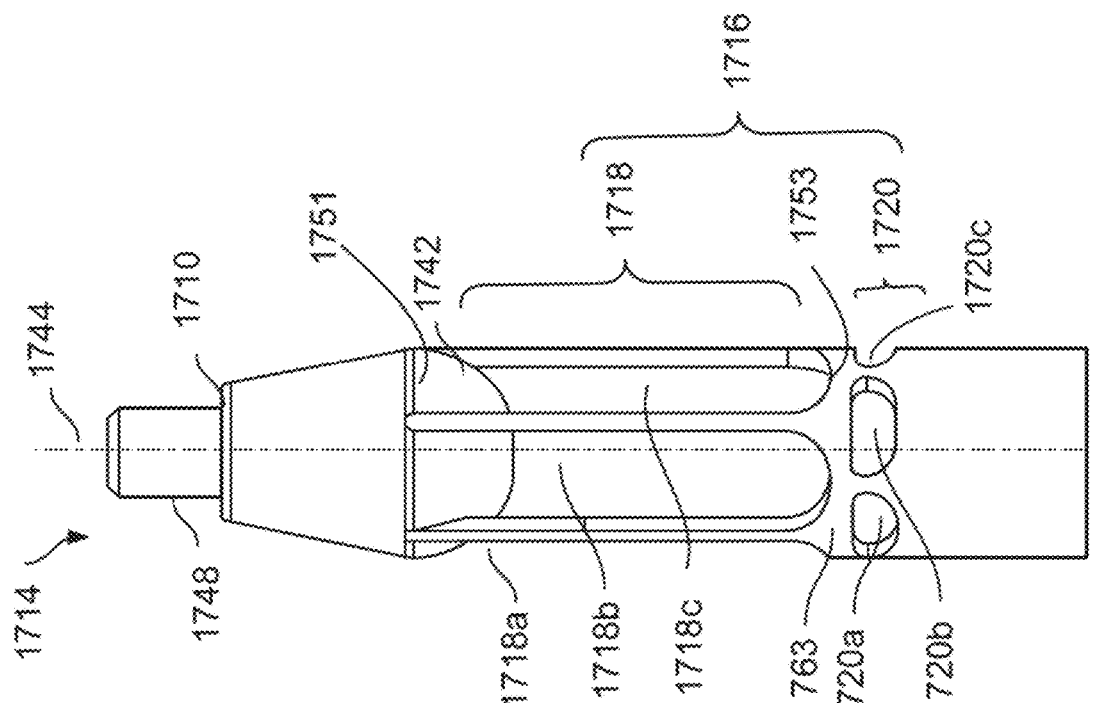
FIG. 17 shows a front view of a distal end portion of a heart pump assembly having an alternative arrangement of apertures positioned in a first ring of long apertures and a second ring of shorter apertures, in accordance with example implementations.

FIG. 17 shows a front view of a distal end portion 1714 of a cannula assembly having a plurality of apertures 1716 arranged into two rings of apertures according to certain implementations. The distal end portion 1714 includes a distal end 1710, an atraumatic tip connector 1748, a tear drop portion 1742, a longitudinal axis 1744, a plurality of apertures 1716, and a circumferential strut 1763. The circumferential strut 1763 runs about a circumference of the distal end portion 1714 and divides the plurality of apertures 1716 into rings of apertures. The plurality of apertures 1716 are disposed in a first ring 1718 of apertures 1718a-c, and a second ring 1720 of apertures 1720a-c. The circumferential strut 1763 divides the first ring 1718 from the second ring 1720. The shape of the apertures 1718a-c of the first ring 1718 may be the same oblong shape defined at a distal edge 1751 by the tear drop portion 1742 as in FIGS. 14-16. The size and shape of the apertures 1720a-c of the second ring 1720 may be the same as in FIGS. 14-16. The apertures 1718a-c of the first ring 1718 and the apertures 1720a-c of the second ring 1720 are shown offset from one another. However, in some implementations, the apertures 1718a-c of the first ring 1718 are rotationally aligned with the apertures 1720a-c of the second ring 1720.

FIG. 18 shows a front view of a distal end portion 1814 of a cannula assembly having a plurality of apertures 1816 arranged into two rings of apertures according to certain implementations. The distal end portion 1814 of the cannula 1808 includes a distal end 1810, an atraumatic tip connector 1848, a tear drop portion 1842, a plurality of apertures 1816, and a circumferential strut 1863. The circumferential strut 1863 runs about a circumference of the distal end portion 1814 and divides the plurality of apertures 1816 into rings of apertures. The plurality of apertures 1816 are arranged into a first ring 1818 having apertures 1818a-c and a second ring 1820 having apertures 1820a-c. The circumferential strut 1863 divides the first ring 1818 from the second ring 1820. The apertures 1818a-c of the first ring 1818 are defined on one side by the tear drop portion 1842 and have a lesser height than the apertures 1718a-c of the distal end portion of FIG. 17. The area through which blood may enter the cannula assembly 1808 may be decreased in FIG. 18 as compared to FIG. 17. However, the circumferential strut 1863 1820 is greater in FIG. 18 than circumferential strut 1763 in FIG. 17. This increases the area over which there is no suction and may decrease the likelihood of suctioning a valve leaflet or other tissue to the cannula assembly.

FIGS. 19-23 show arrangements according to various implementations in which a distal end portion includes a plurality of apertures arranged in four rings. For example, FIG. 19 shows a front view of a distal end portion 1914 of a cannula assembly. The distal end portion 1914 includes a distal end 1910, an atraumatic tip connector 1948, a tear drop portion 1942, a longitudinal axis 1944, a plurality of apertures 1916, a first circumferential strut 1963, a second circumferential strut 1965, and a third circumferential strut 1967. The circumferential struts 1963, 1965, and 1967 run about a circumference of the distal end portion 1914 and divide the plurality of apertures 1916 into rings of apertures. The plurality of apertures 1916 is disposed in a first ring 1918 of apertures 1918a-c, a second ring 1920 of apertures 1920a-c, a third ring 1930 of apertures 1930a-c, and a fourth ring 1940 of apertures 1940a-c. The first circumferential strut 1963 divides the first ring 1918 from the second ring 1920. The second circumferential strut 1965 divides the second ring 1920 from the third ring 1930. The third circumferential strut 1967 divides the third ring 1930 from the fourth ring 1940. The apertures 1918a-c are defined on one side by the tear drop portion 1942. The respective heights of the apertures 1918a-c of the first ring 1918, the apertures 1920a-c of the second ring 1920, the apertures 1930a-c of the third ring 1930, and the apertures 1940a-c of the fourth ring 1940 are similar. The first circumferential strut 1963 has a similar height as the second circumferential strut 1965 which is also similar to a height of the third circumferential strut 1967. The area of the apertures 1918a-c of the first ring 1918 is similar to the areas of the apertures 1920a-c of the second ring 1920, the apertures 1930a-c of the third ring 1930, and the apertures 1940a-c of the fourth ring 1940. Though the apertures in the second ring 1920, the third ring 1930, and the fourth ring 1940 are shown in alignment with the apertures 1918a-c of the first ring, in some implementations the apertures can also be rotationally offset.

FIG. 20 shows a front view of a distal end portion 2014 of a cannula assembly 2008 having a plurality of apertures 2016 in which each ring of apertures has a different size and shape according to certain implementations. The distal end portion 2014 includes a distal end 2010, an atraumatic tip connector 2048, a tear drop portion 2042, a longitudinal axis 2044, and a plurality of apertures 2016. The plurality of apertures 2016 are disposed in a first ring 2018 of apertures 2018a-c, a second ring 2020 of apertures 2020a-b, a third ring 2030 of apertures 2030a-b, and a fourth ring 2040 of apertures 2040a-b. The apertures 2018a-c are defined on one side by the tear drop portion 2042. The apertures 2018a-c of the first ring 2018 have the greatest height of the plurality of apertures 2016. The apertures 2020a-b of the second ring 2020 have the next greatest height. The apertures 2030a-b of the third ring 2030 have the next greatest height. The apertures 2040a-b of the fourth ring 2040 are the smallest in height of the plurality of apertures 2016. The plurality of apertures 2016 are shown having rounded shapes; however, the plurality of apertures 2016 may have any suitable shape while maintaining the relationship between the heights. In some implementations, the height the apertures 2018a-c of the first ring 2018 is less than six times the height of the apertures 2020a-b of the second ring 2020. In some implementations, the height of the apertures 2020a-b of the second ring 2020 is less than three times the height of the apertures 2030a-b of the third ring 2030. In some implementations, the height of the apertures 2030a-b of the third ring 2030 is less than five times the height of the apertures 2040a-b of the fourth ring 2040.

In each of FIGS. 21-22 the apertures of the first ring have the same oblong shape and same size, and the apertures of the second, third and fourth rings have the same size and shape. In FIG. 21, a distal end portion 2114 includes a distal end 2110, an atraumatic tip connector 2148, a tear drop portion 2142, a longitudinal axis 2144, and a plurality of apertures 2116. The plurality of apertures 2116 are disposed in a first ring 2118 of apertures 2118a-c, a second ring 2120 of apertures 2120a-c, a third ring 2130 of apertures 2130a-c, and a fourth ring 2140 of apertures 2140a-c. The apertures 2118a-c of the first ring 2118 are oblong. In particular, the first ring 2118 of apertures 2118a-c are rounded on a proximal edge 2153 and have a distal edge 2151 defined by a portion 2152 of tear drop portion 2142. The apertures 2120a-c in the second ring 2120 are the same shape and size as the apertures 2130a-c in the third ring 2130 and as the apertures 2140a-c in the fourth ring 2140. The plurality of apertures 2116 in the second ring 2120, the third ring 2130, and the fourth ring 2140 are oblong, each having a width which is greater than a height as measured along a line parallel to the longitudinal axis 2144. The plurality of apertures 2116 in the second ring 2120, the third ring 2130, and the fourth ring 2140 are rounded at their proximal edges 2169a-c with the centers of the proximal edges 2153 and 2169a-c being the proximal-most point of each aperture. Each aperture has an inner edge 2171a-d. The inner edge 2171a-d of each of the plurality of apertures 2116 is chamfered. The chamfer may be at an angle of 45 degrees or less relative to a line normal to the surface of the cannula assembly 108. In some implementations, the chamfered inner edge 2171a-d includes a chamfer of 10·degree, 20·degree, 30·degree, 40·degree, 50·degree, >50·degree, or any other suitable angle. The use of a chamfered inner edge 2171a-d can reduce hemolysis of the blood as it enters the cannula assembly 2108. Though the chamfered inner edge 2171a-d is shown here in an arrangement having four rings of apertures, a chamfered inner edge may be used in any of the arrangements shown herein. In FIG. 22, as in FIG. 21, the distal end portion 2214 includes a distal end 2210, an atraumatic tip connector 2248, a tear drop portion 2242, a longitudinal axis 2244, and a plurality of apertures 2216 disposed in a first ring 2218 of apertures 2218a-c, a second ring 2220 of apertures 2220a-c, a third ring 2230 of apertures 2230a-c, and a fourth ring 2240 of apertures 2240a-c. Each of the plurality of apertures 2216 has an inner edge 2271a-d, which is rounded. In some implementations, the rounded inner edge 2271a-d includes a radius ranging from 40 microns to 105 microns. In some implementations, only an outward facing portion of the inner edge 2271a-d is rounded. In some implementations, the rounding of the inner edge 2271a-d is accomplished by polishing. In some implementations, the rounding of the inner edge 2271a-d is accomplished by a tumbling process. Rounded edges may decrease hemolysis of the blood as it enters the cannula assembly 2208 through the plurality of apertures 2216. Though the rounded inner edge 2271a-d is shown here in an arrangement having four rings of apertures, a rounded inner edge may be used in any of the arrangements shown herein.

FIG. 23 shows a front view of a distal end portion 2314 of a cannula assembly. The distal end portion 2314 includes a distal end 2310, an atraumatic tip connector 2348, a tear drop portion 2342, a longitudinal axis 2344, and a plurality of apertures 2316. The plurality of apertures is disposed in a first ring 2318 of apertures 2318a-c, a second ring 2320 of apertures 2320a-c, a third ring 2330 of apertures 2330a-c, and a fourth ring 2340 of apertures 2340a-c. The apertures 2318a-c of the first ring 2318 have an oblong shape defined at a distal edge 2351 by the tear drop portion 2342. The plurality of apertures 2320a-c, 2330a-c, and 2340a-c of the second ring 2320, third ring 2330, and fourth ring 2340, respectively, are oval in shape such that a width is larger than a height, and all of the plurality of apertures in the second ring 2320, third ring 2330, and fourth ring 2340 are the same size.

Figure 24:
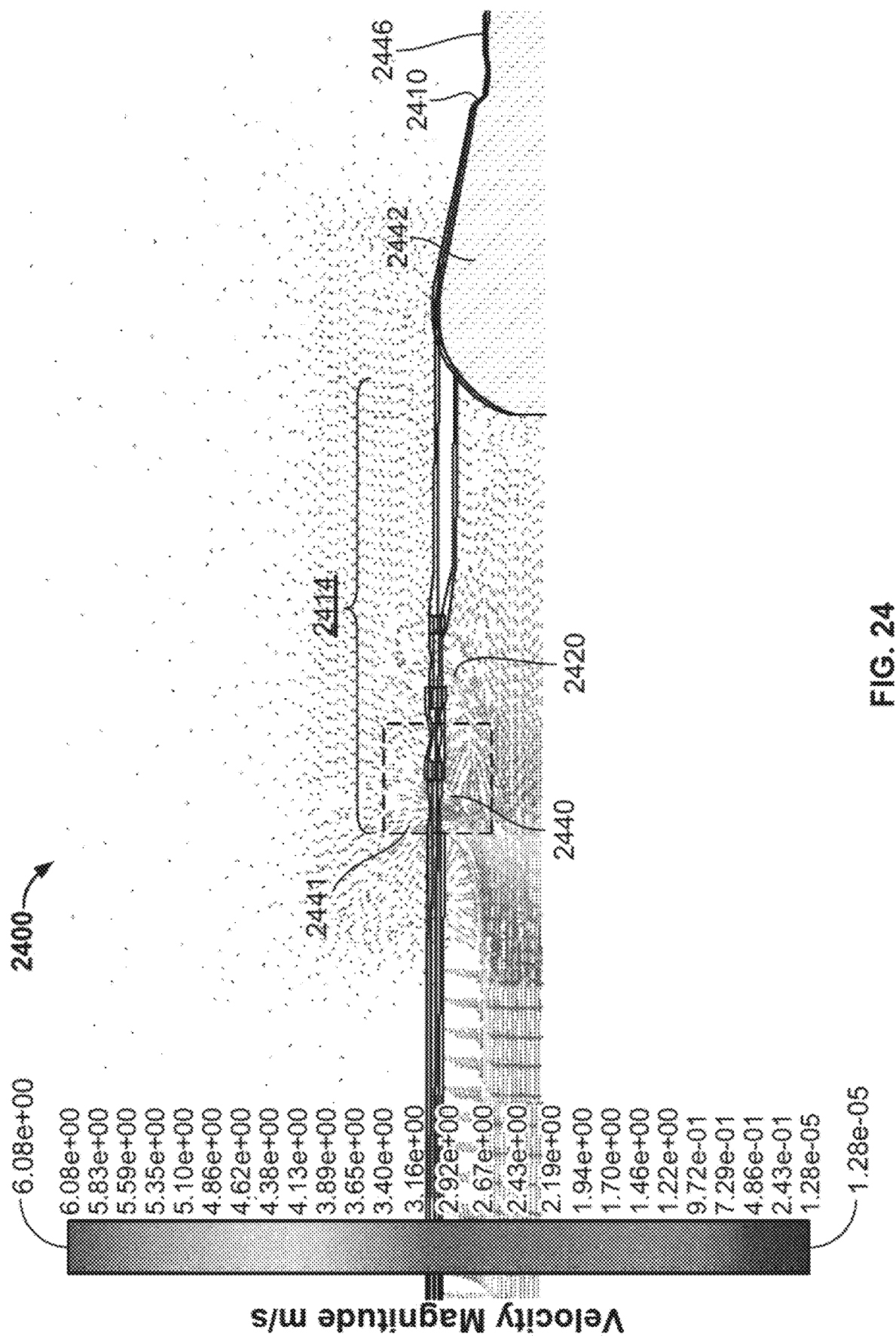
FIG. 24 shows a plot displaying the predicted flow rate of a fluid through the plurality of apertures in an example arrangement, in accordance with example implementations.

FIG. 24 shows a plot 2400 displaying a predicted flow of fluid through the plurality of apertures to the arrangement of FIG. 23. The plot 2400 includes a cut-away of a distal end portion 2414 of a cannula assembly, a second aperture 2420, a fourth aperture 2440, and a box 2441 indicating a region of high flow. The plot shows the predicted flow of fluid through two apertures of a heart pump as shown in cross-section. The heart pump has a first, second, third, and fourth ring of apertures, though only an aperture of the second ring 2420 and fourth ring 2440 are visible, as the first ring 2418 and third ring 2430 are rotationally offset in the depicted implementation. Areas of higher velocities in the plot are depicted with longer lines, while areas of lower flow are shown with fewer lines. The velocity magnitude of the fluid flow ranges from $1.28 \cdot \text{times} \cdot e^{-05}$ m/s (about 0 m/s) to 6.08 m/s. The highest volumetric flow rate (highlighted by the box 2441) occurs at the most proximal apertures, in this case through the aperture 2440a of the fourth ring 2440. The high inflow of fluid into the cannula assembly 2408 at this point is due to the relatively higher-pressure gradient at this aperture. The blood is pulled from outside of the cannula assembly 2408, through the apertures and into the cannula assembly 2408 where the blood flows to the downstream apertures (not shown).

Figure 25:
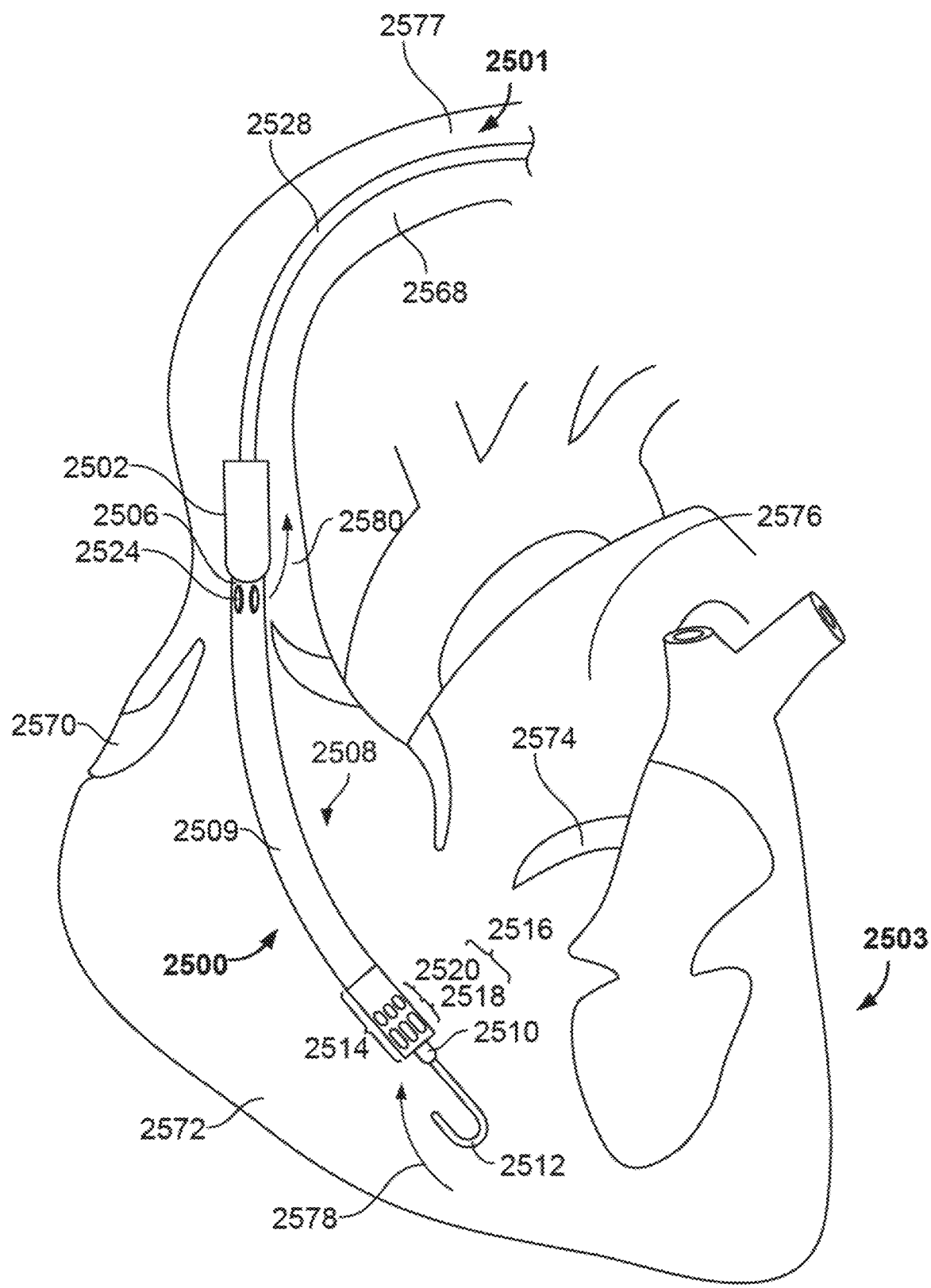
FIG. 25 shows a percutaneous pump having a plurality of apertures at a distal end portion inserted into a blood vessel of a patient, in accordance with example implementations.

FIG. 25 shows a percutaneous heart pump assembly 2500 having a plurality of apertures 2516 at a distal end portion 2514 inserted into a blood vessel 2501 of a patient. In particular, the heart pump assembly 2500 is introduced through a blood vessel 2501 of a patient and into a heart 2503. The heart 2503 includes an aorta 2568, aortic arch 2577, aortic valve 2570, left ventricle 2572, left atrium 2576, and mitral valve 2574, as well as other structures. The heart pump assembly 2500 includes a catheter 2528, a motor housing 2502, a cannula assembly 2508, a cannula body 2509, a distal end portion 2514, a proximal end 2506, a distal end 2510, an atraumatic tip 2512, a plurality of apertures 2516, and a plurality of blood exhaust outlets 2524. The motor housing 2502 of the heart pump assembly 2500 is connected to a motor (not shown). The motor is internal to and integrated with the motor housing 2502. In other implementations the motor is external to the body and connected to the pump via a drive shaft (not shown) within a catheter 2528 and in such an example the assembly 2508 may not include the motor housing 2502. The cannula assembly 2508 is connected to a distal end of the motor housing 2502. The distal end portion 2514 of the cannula assembly 2508 includes the plurality of apertures 2516 through which blood may enter the cannula assembly 2508. The plurality of apertures 2516 are arranged into at least a first ring 2518 and a second ring 2520 of apertures which are radially oriented and disposed about a circumference of the cannula assembly 2508. Though two rings of apertures are depicted here, any arrangement of apertures described herein may be used. In some implementations, the plurality of apertures 2516 is arranged into three, four, or more rings of apertures. The atraumatic tip 2512 is coupled to the distal end 2510 of the cannula assembly 2508, distal of the plurality of apertures 2516. Blood is pulled into the cannula assembly 2508 at the plurality of apertures 2516 along path 2578. The blood passes through the cannula assembly 2508 and exits at the plurality of blood exhaust outlets 2524 proximal to the motor housing 2502 via path 2580.

The heart pump assembly 2500 may be introduced percutaneously during a cardiac procedure through the vascular system. Specifically, the heart pump assembly 2500 can be inserted percutaneously via a catheterization procedure through the femoral artery, into the ascending aorta 2568, across the aortic valve 2570 and into the left ventricle 2572. The heart pump assembly 2500 can be positioned in a heart 2503 of a patient such that the heart pump assembly is inserted over the aortic arch 2577. The plurality of blood exhaust outlets 2524 may be positioned in the aorta 2568 above the aortic valve 2570. The cannula assembly 2508 is positioned across the aortic valve 2570 such that the plurality of apertures 2516 through which blood enters is placed in the left ventricle 2572 of the heart 2503. The atraumatic tip 2512 spaces the cannula assembly 2508 from the walls of the heart 2503 and prevents the plurality of apertures 2516 from suctioning to the walls of the heart 2503.

In some instances, however, the positioning of the heart pump assembly 2500 places the plurality of apertures 2516 near the mitral valve leaflets 2574 at the entrance to the left atrium 2576. This may be due to the individual anatomy of the particular heart 2503. The mitral valve leaflets 2574 may be sucked by the suction of the pump towards the plurality of apertures 2516 and may become suctioned to some of the plurality of apertures 2516, blocking the inflow of blood through the plurality of apertures 2516. In some instances, in particular in pumps with large inlets, for example heart pump assembly 100 in FIG. 1, the mitral valve leaflets 2574 can be sucked through one of the plurality of apertures 2516 into the cannula assembly 2508 where the mitral valve leaflet 2574 blocks blood flow through the cannula. A plurality of apertures 2516 of a smaller size prevents the suctioning of the mitral valve leaflets to the plurality of apertures 2516. Furthermore, the plurality of apertures 2516 allows blood flow through the cannula assembly 2508 to be maintained despite suction of the mitral valve leaflet 2574 or other tissue or debris to some of the plurality of apertures 2516. In another embodiment (not shown) the heart pump assembly may be designed to support a patient's right heart. In certain aspects, the device may be inserted percutaneously through the femoral vein, into the right atrium or inserted via other techniques. With the device so positioned, the cannula of the assembly may extend across the tricuspid and pulmonic valves, and into the pulmonary artery. In this case, the plurality of apertures can be located on the inlet of the pump which is positioned in the inferior vena cava (IVC). As will be appreciated, such a device can include any of the configurations of apertures described above. The device may or may not include an atraumatic tip or projection.

Figure 26:
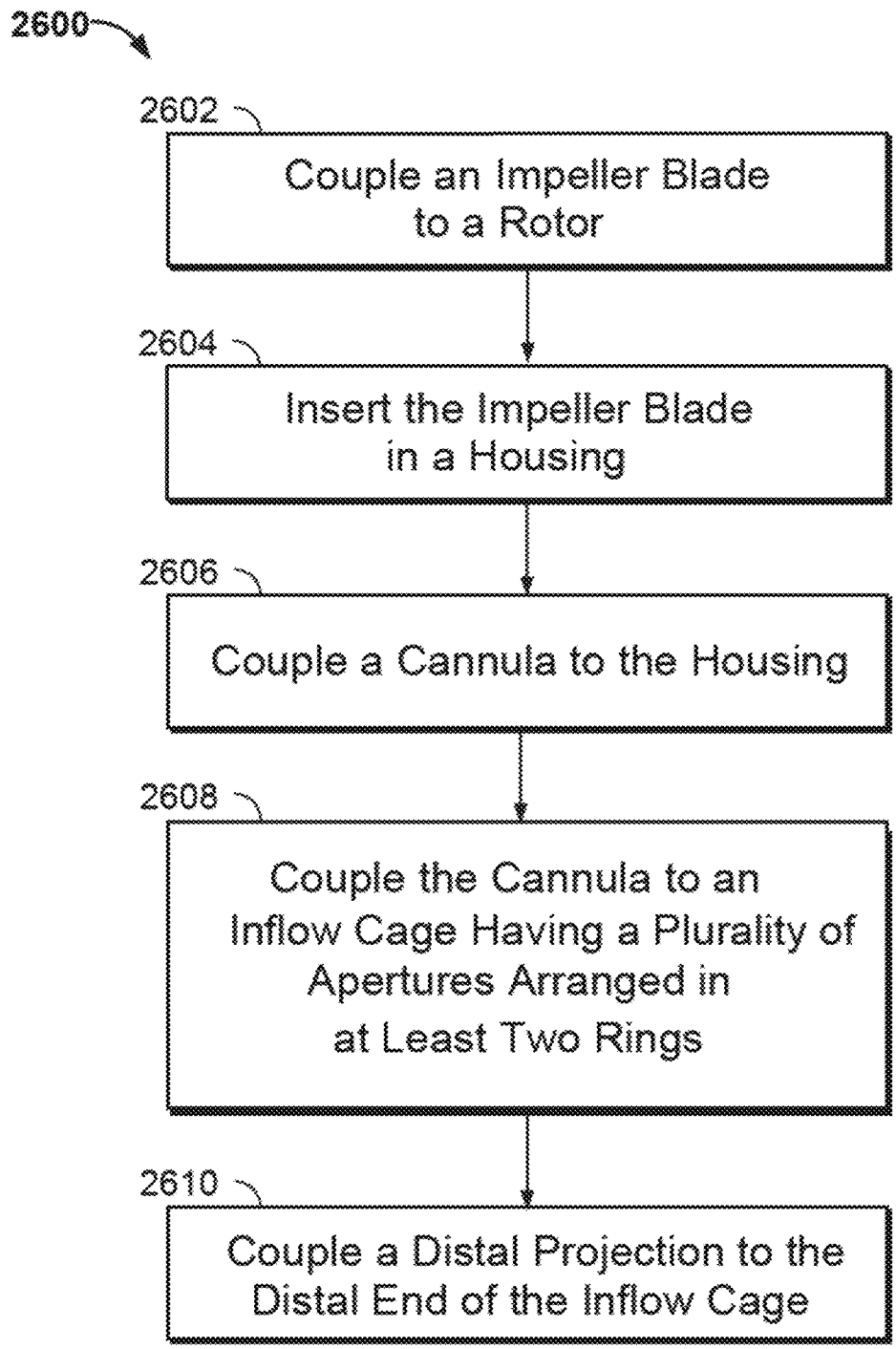
FIG. 26 is a flow chart of a method for manufacturing a heart pump having a plurality of apertures at a distal end portion, in accordance with example implementations.

FIG. 26 is a flow chart of a method for manufacturing a heart pump (e.g., heart pump assembly 200 of FIG. 2, heart pump assembly 400 of FIG. 4, heart pump assembly 2500 of FIG. 25, or any other suitable heart pump) having a plurality of apertures at a distal end portion, according to certain implementations. The method 2600 may be implemented to form a heart pump having any number of apertures at the distal end portion, disposed in any number of rings. The method 2600 may be implemented for manufacture of a heart pump assembly having apertures of any size or shape with straight, chamfered or rounded edges. In step 2602 an impeller blade is coupled to a rotor of a motor. The impeller blade may have any suitable number of blades and may be rotated by a drive shaft connected to a motor. In some implementations, the motor is configured to be external to a patient during operation of the pump. In some implementations, the motor is integrated with the motor housing. In step 2604, the impeller blade is inserted into a motor housing. In step 2606, a cannula is coupled to the motor housing. The cannula may be attached to a distal end of the motor housing. In some implementations, the cannula is expandable. In some implementations, the cannula is self-expandable. In some implementations, the cannula may be comprised of a mesh, such as a nitinol mesh, covered by an elastic covering.

In some implementations, the cannula may be comprised of a solid wire such as nitinol wire with a polymer cover or fabric.

In step 2608, the cannula is coupled to an inflow cage which comprises a plurality of apertures. In some implementations, the inflow cage is comprised of stainless steel. The plurality of apertures may be of any number, shape, or size which is suitable for the passage of blood through the apertures in the inflow cage and into the cannula. The plurality of apertures is radially oriented about a circumference of the inflow cage. The plurality of apertures is arranged into at least a first ring of apertures and a second ring of apertures proximal of the first ring of apertures. The number of apertures in a ring is 3, 4, 5, 6, 7, 8, 9, 10 or any other suitable number of apertures. In some implementations, the number of apertures in the first ring is the same as the number of apertures in the second ring. The first ring of apertures extends to an end of the distal end portion of the inflow cage. In some implementations, the plurality of apertures additionally has more rings, including a third ring proximal of the second ring and a fourth ring proximal of the third ring. Each of the plurality of apertures may have an outer edge which in some implementations is formed or altered by a tumbling process.

The plurality of apertures may have a size, shape, number, or positioning which helps to prevent the suction of heart tissues including valve leaflets onto or into the plurality of apertures which blocks the inflow of blood to the pump, limiting efficiency of the heart pump. For example, in some implementations, the height of the first apertures is less than 9 mm. In some implementations, the height of the aperture of the first ring is 0.5 mm, 1 mm, 3 mm, 5 mm, 6 mm, 9 mm, 10 mm, 12 mm, 15 mm or any other suitable height. In some implementations, the height of the second aperture is less than 3 mm. In some implementations, the height of the aperture of the second ring is 0.25 mm, 0.5 mm, 1 mm, 1.5 mm, 2 mm, 2.5 mm, 3 mm, 3.5 mm, 4 mm, 5, mm, 6 mm, or any other suitable height. In some implementations, a width of the second aperture is less than 4 mm. In some implementations, the width of the apertures of the second ring is 0.5 mm, 1 mm, 1.5 mm, 2 mm, 2.5 mm, 3 mm, 3.5 mm, 4 mm, 5, mm, 6 mm, 8 mm, or any other suitable width. In some implementations, a height and width of an aperture in the third ring is the same as the height and width of an aperture in the second ring.

The area of each aperture may vary. In some implementations, the area of an aperture in the first ring is greater than the area of apertures in other rings. In some implementations, the area of the first aperture is less than 20 $mm^2$. In some implementations, the area of the aperture of the first ring is 0.5 $mm^2$, 1 $mm^2$, 5 $mm^2$, 10 $mm^2$, 15 $mm^2$, 18 $mm^2$, 20 $mm^2$, 23 $mm^2$, 25 $mm^2$ or any other suitable area. The area of aperture of the second ring may be less than 12 $mm^2$. In some implementations, the area of the apertures of the second ring may be 0.25 $mm^2$, 0.5 $mm^2$, 1 $mm^2$, 2 $mm^2$, 5 $mm^2$, 10 $mm^2$, 12 $mm^2$, or any other suitable area.

The apertures may have inner edges which are straight, rounded or chamfered. In some implementations, the apertures have at least one chamfered edge. The chamfer may be at an angle of 45 degrees or less relative to a line normal to the surface of the inflow cage. In some implementations, the chamfered inner edge includes a chamfer of 10-degree, 20-degree, 30-degree, 40-degree, 50-degree, >50-degree, or any other suitable angle. The use of a chamfered inner edge can reduce hemolysis of the blood as it enters the inflow cage. In some implementations, the apertures have at least one rounded edge. In some implementations, the rounded inner edge includes a radius ranging from 40 microns to 105 microns.

In some implementations, the plurality of apertures is formed in a distal end portion of the cannula. In some implementations, the distal end portion of the cannula is comprised of stainless steel. The plurality of apertures formed in the cannula may be of any number, shape, or size which is suitable for the passage of blood through the apertures and into the cannula. The plurality of apertures may be radially oriented about a circumference of the cannula. The plurality of apertures is arranged into at least a first ring of apertures and a second ring of apertures proximal of the first ring of apertures. The number of apertures in a ring is 3, 4, 5, 6, 7, 8, 9, 10 or any other suitable number of apertures. In some implementations, the number of apertures in the first ring is the same as the number of apertures in the second ring. The first ring of apertures extends to an end of the distal end portion of the cannula. In some implementations, the plurality of apertures additionally has more rings, including a third ring proximal of the second ring and a fourth ring proximal of the third ring. Each of the plurality of apertures may have an outer edge which in some implementations is formed or altered by a tumbling process.

In step 2610, a distal projection is coupled to the distal end of the inflow cage. The distal projection or atraumatic tip is distal to the plurality of apertures. A base of the distal projection may form a distal edge of the plurality of apertures in the first ring of apertures. In some implementations, this step is optional and no distal projection is attached to the heart pump. In some implementations, the distal projection is configured as a pigtail. In some implementations, the distal projection is configured as a flexible projection or extension. The distal projection is an atraumatic tip configured to space the plurality of apertures on the inflow cage away from a wall of the heart. In some implementations, the distal projection includes a lumen through which a guidewire may be inserted. The distal projection provides mechanical lengthening of the cannula in order to prevent suction at the plurality of apertures to the tissues of the heart.

Figure 27:
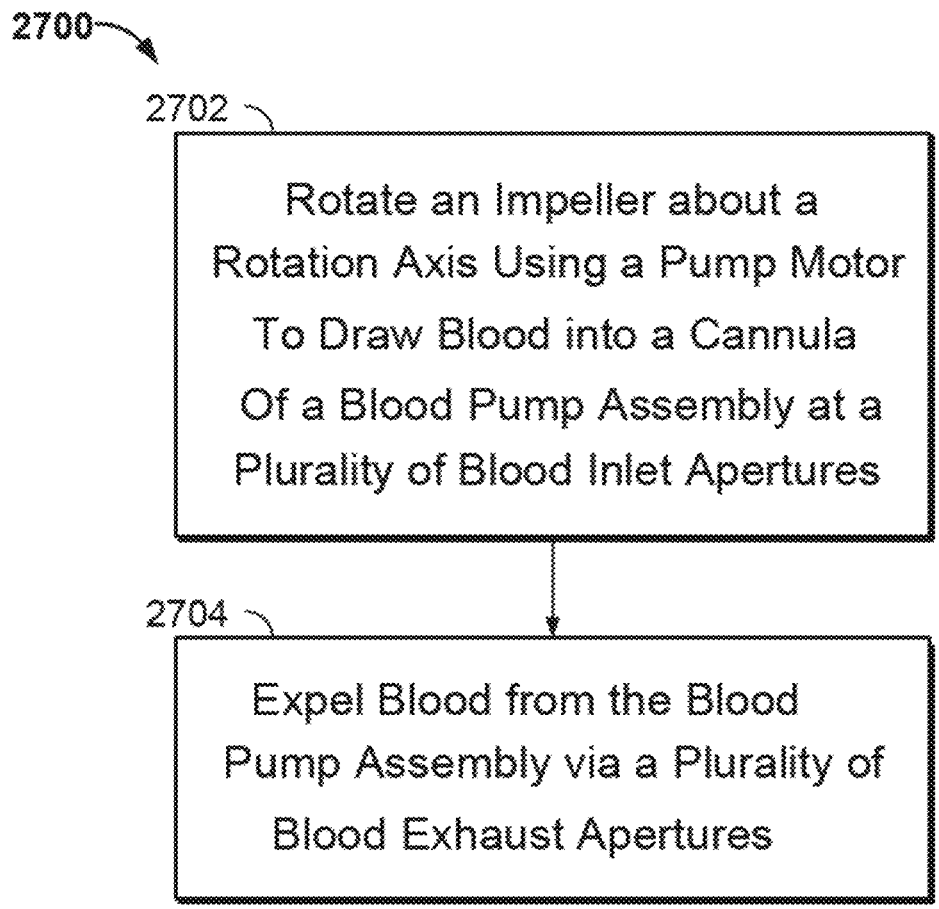
FIG. 27 is a flow chart of a method for use of a heart pump having a plurality of apertures at a distal end portion, in accordance with example implementations.

FIG. 27 shows a flow chart of a method for use of a heart pump (e.g., heart pump assembly 200 of FIG. 2, heart pump assembly 400 of FIG. 4, heart pump assembly 2500 of FIG. 25, or any other suitable heart pump) having a plurality of apertures at a distal end portion. The method 2700 may be implemented to form a heart pump having any number of apertures at the distal end portion, disposed in any number of rows. The method 2700 may be implemented for use of a heart pump assembly having apertures of any size or shape with straight, chamfered or rounded edges. In step 2702, an impeller is rotated about a rotation axis using a pump motor to draw blood into a cannula of a heart pump assembly at a plurality of blood inlet apertures. The motor may be external to a patient and connected to the impeller by a drive shaft. Alternatively, the motor may be integrated into the pump and used internally. The blood inlet apertures may have any size, shape or number. The blood inlet apertures are radially oriented about a circumference of the cannula and are arranged in at least two rings at a distal end portion of the cannula. The size, shape, number, and position of the blood inlet apertures can be configured to decrease the occurrence of suctioning of heart tissues, valve leaflets and other debris to block the inlet apertures.

In step 2704, the blood is expelled from the heart pump assembly at a plurality of blood exhaust apertures disposed at a proximal end portion of the cannula proximal to the motor housing. The blood may be sucked into the cannula at the blood inlet apertures in the left ventricle and may be expelled from the blood exhaust apertures into the aorta above the aortic valve. The plurality of small inflow apertures prevents or reduces the tendency of the aperture to suck against heart structures or valve leaflets. The small apertures prevent the pump from sucking a leaflet into the inlet, allowing the pump to provide more assistance to the heart and decreasing potential damage to heart structures which may be suctioned to the pump.

The foregoing is merely illustrative of the principles of the disclosure, and the apparatuses can be practiced by other than the described embodiments, which are presented for purposes of illustration and not of limitation. It is to be understood that the apparatuses disclosed herein, while shown for use in percutaneous heart pumps, may be applied to apparatuses in other applications requiring a clear aperture for inflow.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A heart pump assembly comprising:
   a rotor;
   a motor coupled to the rotor;
   an impeller blade coupled to the rotor such that rotation of the rotor causes the impeller blade to rotate and pump blood;
   a catheter; and
   a cannula assembly comprising a cannula body and a blood inlet including a plurality of apertures radially oriented and disposed about a constant circumference exterior portion of the blood inlet,
   wherein the impeller blade is inside the cannula assembly, and
   wherein the plurality of apertures are open and configured to allow the blood to enter or exit and include at least a first row of apertures spaced apart linearly about the constant circumference exterior portion of the blood inlet and a second row of apertures spaced laterally from the first row of apertures on the constant circumference exterior portion of the blood inlet, wherein the second row of apertures are proximal of the first row of apertures such that the second row of apertures are closer to the catheter than the first row of apertures, and
   wherein the first row of apertures includes a plurality of first apertures and the second row of apertures includes a plurality of second apertures, each of the plurality of first apertures having an area greater than an area of each of the plurality of second apertures.

2. The heart pump assembly of claim 1, wherein the area of each of the plurality of first apertures is at least two times greater than the area of each of the plurality of second apertures.

3. The heart pump assembly of claim 2, wherein each of the plurality of first apertures has a height measured parallel to a longitudinal axis of the cannula body that is greater than a height of each of the plurality of second apertures measured parallel to the longitudinal axis of the cannula body.

4. The heart pump assembly of claim 3, wherein the height of each of the plurality of first apertures is at least two times greater than the height of each of the plurality of second apertures.

5. The heart pump assembly of claim 1, further comprising a third row of apertures proximal of the second row of apertures.

6. The heart pump assembly of claim 5, further comprising a fourth row of apertures proximal of the third row of apertures.

7. The heart pump assembly of claim 6, wherein a height of each of the plurality of first apertures is greater than a height of each of a plurality of third apertures of the third row of apertures or a height of each of a plurality of fourth apertures of the fourth row of apertures.

8. The heart pump assembly of claim 7, wherein the height of each of the plurality of first apertures is less than 9 mm.

9. The heart pump assembly of claim 8, wherein the height of each of the plurality of second apertures is less than 3 mm.

10. The heart pump assembly of claim 9, wherein the area of each of the plurality of first apertures is less than 20 mm$^2$.

11. The heart pump assembly of claim 7, wherein the plurality of first apertures in the first row of apertures and the plurality of third apertures in the third row of apertures are aligned along an axis on an outer surface of the cannula body parallel to a longitudinal axis of the cannula body.

12. The heart pump assembly of claim 11, wherein the plurality of second apertures in the second row of apertures and the plurality of fourth apertures in the fourth row of apertures are aligned along the axis on the outer surface of the cannula body parallel to the longitudinal axis of the cannula body.

13. The heart pump assembly of claim 1, wherein the plurality of apertures is formed near a terminal end of the cannula assembly.

14. The heart pump assembly of claim 1, wherein each of the plurality of apertures is defined by an inner edge intersecting an interior of the cannula body and an outer edge intersecting an outer surface of the cannula body, and wherein the outer edge of each of the plurality of apertures is rounded.

15. The heart pump assembly of claim 1, wherein each of the plurality of apertures is defined by an inner edge intersecting an interior of the cannula body and an outer edge intersecting an outer surface of the cannula body, and wherein the outer edge of each of the plurality of apertures is chamfered.

16. The heart pump assembly of claim 1, wherein the heart pump assembly is sized for percutaneous insertion.

* * * * *